United States Patent
Dieterle et al.

(10) Patent No.: US 8,394,345 B2
(45) Date of Patent: Mar. 12, 2013

(54) PROCESS FOR PREPARING AT LEAST ONE ORGANIC TARGET COMPOUND BY HETEROGENEOUSLY CATALYZED GAS PHASE PARTIAL OXIDATION

(75) Inventors: Martin Dieterle, Mannheim (DE); Klaus Joachim Mueller-Engel, Stutensee (DE); Jochen Petzoldt, Weisenheim am Berg (DE); Ulrich Hammon, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 586 days.

(21) Appl. No.: 12/146,807

(22) Filed: Jun. 26, 2008

(65) Prior Publication Data

US 2008/0260605 A1   Oct. 23, 2008

Related U.S. Application Data

(62) Division of application No. 11/357,300, filed on Feb. 21, 2006, now Pat. No. 7,439,389.

(60) Provisional application No. 60/656,881, filed on Mar. 1, 2005, provisional application No. 60/670,289, filed on Apr. 12, 2005.

(30) Foreign Application Priority Data

Mar. 1, 2005 (DE) .................. 10 2005 009 882
Apr. 12, 2005 (DE) .................. 10 2005 017 050

(51) Int. Cl.
   *B01J 8/10* (2006.01)
(52) U.S. Cl. .................. 422/600; 422/608; 422/614
(58) Field of Classification Search .................. 422/189, 422/190, 196, 197
   See application file for complete search history.

(56) References Cited

U.S. PATENT DOCUMENTS

| | | | |
|---|---|---|---|
| 3,119,837 A | 1/1964 | Kingsley et al. | |
| 3,702,259 A | 11/1972 | Nielsen | |
| 3,799,886 A | 3/1974 | Felice et al. | |
| 3,956,377 A | 5/1976 | Dolhyj et al. | |
| 4,077,912 A | 3/1978 | Dolhyj et al. | |
| 4,408,079 A | 10/1983 | Merger et al. | |
| 4,496,770 A | 1/1985 | Duembgen et al. | |
| 5,173,468 A | 12/1992 | Boehning et al. | |

(Continued)

FOREIGN PATENT DOCUMENTS

| | | |
|---|---|---|
| DE | 1 254 137 | 11/1967 |
| DE | 2 025 430 | 12/1971 |

(Continued)

OTHER PUBLICATIONS

Hans Beyer, "Textbook of organic chemistry", 17$^{th}$ edition, 1973, pp. 259-272.

(Continued)

*Primary Examiner* — Walter D Griffin
*Assistant Examiner* — Lessanework Seifu
(74) *Attorney, Agent, or Firm* — Oblon, Spivak, McClelland, Maier & Neustadt, L.L.P.

(57) ABSTRACT

A process for preparing an organic target compound by heterogeneously catalyzed gas phase partial oxidation of an organic precursor compound with molecular oxygen in two oxidation reactor lines operated in parallel and removal of the target compound from the mixture of the product gas streams in a workup line, wherein the catalysts charge of one of the oxidation lines comprises a portion of catalyst over which the heterogeneously catalyzed gas phase partial oxidation has already been carried out for longer than over the portions of catalyst of the catalyst charge of the other oxidation reactor line.

8 Claims, 1 Drawing Sheet

U.S. PATENT DOCUMENTS

| | | | |
|---|---|---|---|
| 5,221,767 A | 6/1993 | Boehning et al. | |
| 5,231,226 A | 7/1993 | Hammon et al. | |
| 5,264,625 A | 11/1993 | Hammon et al. | |
| 5,668,077 A | 9/1997 | Klopries et al. | |
| 5,734,068 A | 3/1998 | Klopries et al. | |
| 5,739,391 A | 4/1998 | Ruppel et al. | |
| 5,821,390 A | 10/1998 | Ruppel et al. | |
| 6,410,785 B1 | 6/2002 | Zehner et al. | |
| 6,781,017 B2 | 8/2004 | Machhammer et al. | |
| 2003/0187299 A1 | 10/2003 | Machhammer et al. | |
| 2004/0015013 A1 * | 1/2004 | Hammon et al. | 562/532 |
| 2004/0181083 A1 | 9/2004 | Proll et al. | |
| 2004/0242826 A1 | 12/2004 | Nishimura | |
| 2005/0090628 A1 | 4/2005 | Eck et al. | |
| 2005/0096483 A1 | 5/2005 | Dieterle et al. | |
| 2005/0261517 A1 | 11/2005 | Dieterle et al. | |

FOREIGN PATENT DOCUMENTS

| | | |
|---|---|---|
| DE | 2 159 346 | 6/1972 |
| DE | 2 106 796 | 8/1972 |
| DE | 2 351 151 | 4/1974 |
| DE | 25 26 238 | 1/1976 |
| DE | 40 22 212 A1 | 1/1992 |
| DE | 41 32 263 A1 | 4/1993 |
| DE | 41 32 684 A1 | 4/1993 |
| DE | 43 11 608 A1 | 12/1994 |
| DE | 199 02 562 A1 | 7/2000 |
| DE | 100 28 582 A1 | 12/2001 |
| DE | 100 46 672 A1 | 3/2002 |
| DE | 101 31 297 A1 | 1/2003 |
| DE | 103 36 386 A1 | 3/2004 |
| DE | 103 32 758 A1 | 5/2004 |
| DE | 10 2004 025 445 A1 | 2/2005 |
| DE | 103 50 822 A1 | 6/2005 |
| EP | 0 058 927 A1 | 9/1982 |
| EP | 0 092 097 A1 | 10/1983 |
| EP | 0 372 972 A1 | 6/1990 |
| EP | 0 522 871 A1 | 1/1993 |
| EP | 0 529 853 A2 | 3/1993 |
| EP | 0 608 838 A2 | 8/1994 |
| EP | 0 614 872 A1 | 9/1994 |
| EP | 0 700 714 B1 | 3/1996 |
| EP | 0 700 893 B1 | 3/1996 |
| EP | 0 990 636 A1 | 4/2000 |
| EP | 1 090 684 A1 | 4/2001 |
| EP | 1 106 598 A2 | 6/2001 |
| EP | 1 180 508 A1 | 2/2002 |
| GB | 1 291 354 | 10/1972 |
| GB | 1 346 943 | 2/1974 |
| GB | 1 464 198 | 2/1977 |
| WO | WO 89/07101 | 8/1989 |
| WO | WO 01/96270 A2 | 12/2001 |
| WO | WO 01/96271 A2 | 12/2001 |

OTHER PUBLICATIONS

Niloo Farhad, "Acrylic Acids and Acrylic Esters", SRI International, Process Economics Program, Report No. 6C, Feb. 1987, pp. 27-32, 129 and 131.

* cited by examiner

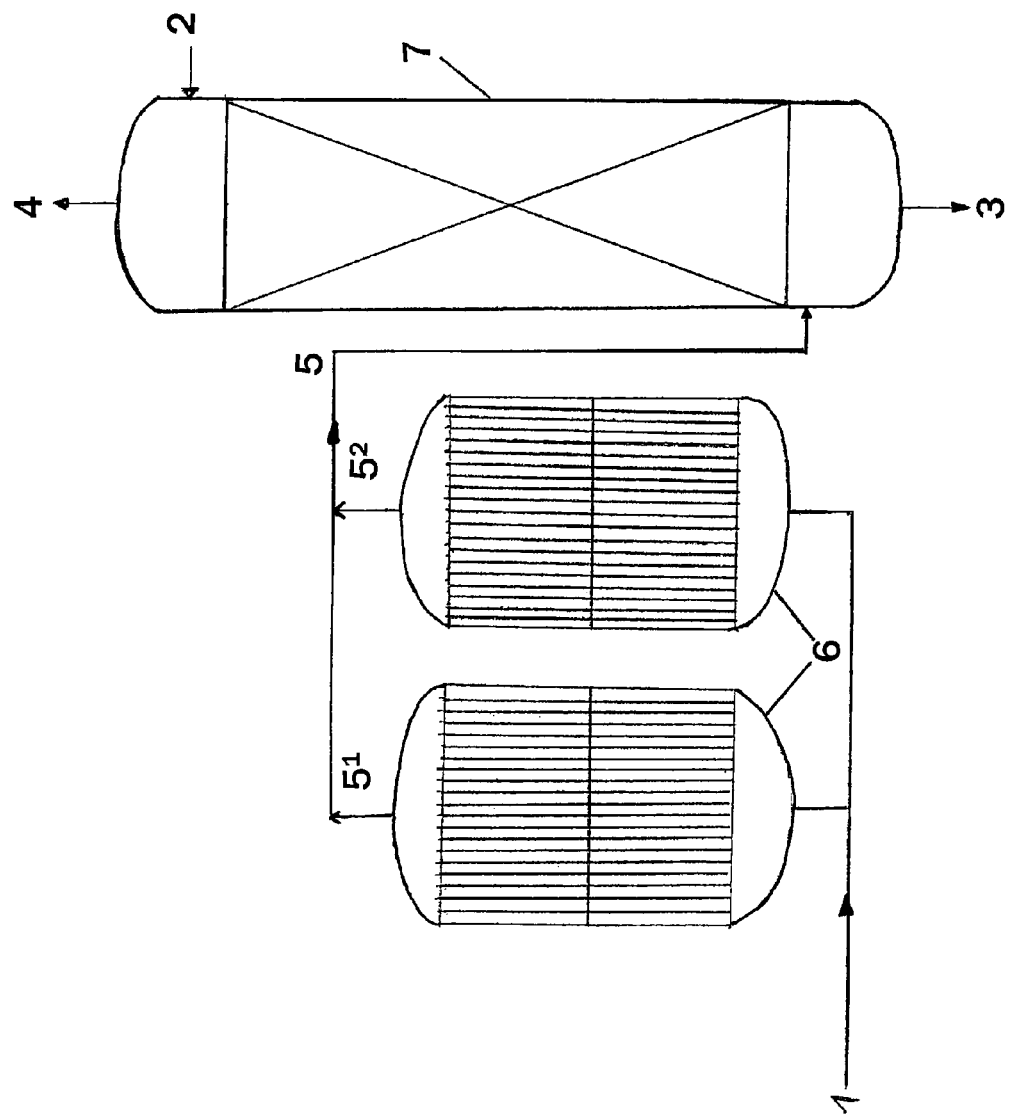

PROCESS FOR PREPARING AT LEAST ONE ORGANIC TARGET COMPOUND BY HETEROGENEOUSLY CATALYZED GAS PHASE PARTIAL OXIDATION

This is a divisional application of U.S. application Ser. No. 11/357,300 filed Feb. 21, 2006, which is a 119(e) of 60/670,289 filed on Apr. 12, 2005 and 60/656,881 filed on Mar. 1, 2005.

DESCRIPTION

The present invention relates to a process for preparing at least one organic target compound by
a) heterogeneously catalyzed gas phase partial oxidation of at least one organic precursor compound with molecular oxygen in at least two oxidation reactor systems which comprise catalyst charges and are operated in parallel to obtain at least two product gas streams each comprising the target compound and each stemming from one of the at least two oxidation reactor systems and
b) subsequent removal of the at least one target compound from the at least two product gas streams to obtain at least one crude target product stream, in which
c) before the removal, mixing together at least two of the at least two product gas streams, or, in the course of the removal, mixing together at least two of any target product-comprising subsequent streams obtained on the route from the at least two product gas mixture streams to the at least one crude target product stream are mixed together, and/or, after the removal from the at least two product gas streams, mixing together any crude target product streams obtained in the course of the removal, to form a mixture stream.

A full oxidation of an organic compound with molecular oxygen is understood here to mean that the organic compound is converted with the reactive action of molecular oxygen in such a way that all of the carbon comprised in the organic compound is converted to oxides of carbon, and all of the hydrogen comprised in the organic compound to oxides of hydrogen.

All different reactions of an organic compound with the reactive action of molecular oxygen are combined here as partial oxidation of an organic compound.

In other words, the concept of partial oxidation in this document shall in particular also comprise partial ammoxidations, which are characterized by the partial oxidative conversion of the organic compound being effected in the presence of ammonia.

In particular, partial oxidations shall be understood here to be those conversions of organic compounds under the reactive action of molecular oxygen in which the organic compound to be oxidized partially (the organic precursor compound), on completion of conversion, comprises at least one more oxygen atom in chemically bound form than before the partial oxidation was carried out.

It is common knowledge that partial and heterogeneously catalyzed oxidation of a wide variety of organic precursor compounds with molecular oxygen in the gas phase allows numerous basic chemicals to be obtained. Examples include the conversion of tertbutanol, isobutene, isobutane, isobutyraldehyde or the methyl ether of tert-butanol to methacrolein and/or methacrylic acid (cf., for example, DE-A 25 26 238, EP-A 092 097, EP-A 058 927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene and/or naphthalene to phthalic anhydride (cf., for example, EP-A 522 871), of m-xylene to isophthalic acid, of p-xylene to terephthalic acid or dimethyl terephthalate, and the conversion of butadiene to maleic anhydride (cf., for example, DE-A 21 06 796 and DE-A 16 24 921), the conversion of n-butane to maleic anhydride (cf., for example, GB-A 1 464 198 and GB 1 291 354), the aforementioned conversions to obtain the acids corresponding to the anhydrides, the conversion of propylene to acrolein and/or acrylic acid (cf., for example, DE-A 23 51 151), the conversion of indanes to, for example, anthraquinone (cf., for example, DE-A 20 25 430), the conversion of ethylene to ethlyene oxide or of propylene to propylene oxide (cf., for example, DE-B 12 54 137, DE-A 21 59 346, EP-A 372 972, WO 89/0710, DE-A 43 11 608 and Beyer, Lehrbuch der organischen Chemie [Textbook of organic chemistry], 17th edition (1973), Hirzel Verlag, Stuttgart, page 261), the conversion of propylene and/or acrolein to acrylonitrile (cf., for example, DE-A 23 51 151), the conversion of isobutene and/or methacrolein to methacrylonitrile, the oxidative dehydrogenation of hydrocarbons (cf., for example, DE-A 23 51 151), the conversion of propane to acrylonitrile, or to acrolein and/or to acrylic acid (cf., for example, DE-A 101 31 297, EP-A 1 090 684, EP-A 608 838, DE-A 100 46 672, EP-A 529 853, WO 01/96270 and DE-A 100 28 582), and also the reactions of ethane to give acetic acid, of benzene to give phenol, and of 1-butene or 2-butene to give the corresponding butanediols, etc.

A disadvantage of the processes for the heterogeneously catalyzed gas phase partial oxidation of organic precursor compounds is that the resulting product gases do not comprise the organic target compound in pure form, but rather as a constituent of a mixture which generally additionally comprises by-products, unconverted reactants and inert diluent gases (in this document, a diluent gas behaving substantially inertly under the conditions of a heterogeneously catalyzed gas phase partial oxidation is understood to mean those diluent gases whose constituents, under the conditions of the heterogeneously catalyzed gas phase partial oxidation, each constituent viewed alone, remain chemically unchanged to an extent of more than 95 mol %, preferably to an extent of more than 99 mol %).

The target compound has to be removed from these product gases/gas mixtures. To this end, the organic target compound is generally transferred from the product gas (gaseous product mixture) initially (if appropriate after completion of direct and/or indirect cooling) to the condensed (liquid and/or solid) phase in apparatus suitable for this purpose. This transfer may be effected, for example, by full or by partial condensation of the product gas. In a preferred embodiment, it is effected by fractional condensation (for example in a column comprising separating internals; cf., for example, DE-A 103 32 758 and prior art cited therein).

Alternatively, the transfer into the condensed phase may also be effected by the target compound from the product gas (mixture) cooled beforehand if appropriate in an absorption apparatus (for example in an absorption column comprising separating internals) being taken up into a suitable liquid absorbent (cf., for example, DE-A 103 36 386, US-A 2004/0242826 and the prior art cited in these documents). The possibility also exists of transferring the organic target compound from the product gas (mixture) into the condensed phase by adsorption on solid adsorption materials or by freezing-out.

Either the condensed phase comprises the target compound (the target product) already in the purity desired for the further use of the target product (in that case, the condensed phase already forms the desired crude target product stream; the prefix "crude" is intended to express that the crude target product stream, in addition to the desired target compound, normally additionally also comprises at least one constituent other than the target product in analytically detectable amounts), or a higher purity of the crude target product stream is desired. In the latter case, the condensed phase merely forms a subsequent stream from which the desired crude target product stream is obtained in a manner known per se by application of further downstream removal processes (connected in series). Such further removal processes are generally extraction and/or rectification separation processes connected in series. If appropriate, these may be supplemented before their use or intermediately by low boiler strippings (low boilers shall be understood to be secondary components whose boiling point under standard conditions (25° C., 1 atm) is below the particular boiling point of the target compound). Moreover, the aforementioned removal processes may be supported by intermediate crystallizative removal processes. Such crystallizative removal processes may also form the sole further purification processes of the condensed phase. The target product-comprising stream conveyed from one purification stage (purification apparatus) to the next purification stage (purification apparatus) in each case forms a subsequent stream in the context of this document. In general, the next subsequent stream obtained in a further purification stage (purification apparatus) from a preceding subsequent stream comprises the target compound in increased purity.

A further feature of the preparation of organic target compounds via heterogeneously catalyzed gas phase partial oxidations of organic precursor compounds with molecular oxygen is that the catalysts to be used in the heterogeneously catalyzed gas phase partial oxidations are normally solids.

Particularly frequently, the catalysts used are oxide compositions or are noble metals (e.g. Ag). The catalytically active oxide composition may comprise, in addition to oxygen, only one other element or more than one other element (multielement oxide compositions). Particularly frequently, the catalytically active oxide compositions used are those which comprise more than one metal, in particular transition metal, element. In this case, they are referred to as multimetal oxide compositions. Typically, multielement oxide compositions are not simple physical mixtures of oxides of the elemental constituents, but rather heterogeneous mixtures of complex poly compounds of these elements.

Furthermore, heterogeneously catalyzed gas phase partial oxidations, in particular the aforementioned, are carried out at elevated temperature (generally a few hundred ° C., typically from 100 to 600° C.).

Since most heterogeneously catalyzed gas phase partial oxidations proceed strongly exothermically, they are carried out for reasons of heat removal appropriately frequently in a fluidized bed or in (usually isothermal) fixed bed reactors, where they are disposed in a reaction chamber around which a heat exchange medium for the purpose of indirect heat exchange is passed (for example, the catalyst bed may be disposed as a fixed bed in the catalyst tubes of a tube bundle reactor, around which a salt melt is passed for heat removal).

In principle, heterogeneously catalyzed gas phase partial oxidations may also be carried out over catalyst beds disposed in adiabatic reactors.

It is known that the working pressure (absolute pressure) in heterogeneously catalyzed gas phase partial oxidations may be below 1 bar, at 1 bar or above 1 bar. In general, it is from 1 to 10 bar, usually from 1 to 3 bar.

The at least one organic precursor compound is converted to the target compound (the target reaction) during the residence time of the reaction gas mixture in the catalyst charge through which it is passed.

Owing to the generally markedly exothermic character of most heterogeneously catalyzed gas phase partial oxidations of organic precursor compounds with molecular oxygen, the reaction partners are typically diluted with a gas which is substantially inert under the conditions of the catalytic partial oxidation in the gas phase and is capable of absorbing the heat of reaction released with its heat capacity.

One of the most frequently used inert diluent gases is molecular nitrogen which is automatically always used when the oxygen source used for the heterogeneously catalyzed gas phase partial oxidation is air.

Owing to its general availability, another inert diluent gas which is used in many cases is steam. In many cases, cycle gas is also used as the inert diluent gas (cf., for example, EP-A 1 180 508). According to the above, the inert diluent gas used in most heterogeneously catalyzed gas phase partial oxidations of organic compounds consists to an extent of $\geq 90\%$ by volume, frequently to an extent of $\geq 95\%$ by volume, of $N_2$, $H_2O$ and/or $CO_2$. The inert diluent gases used are firstly helpful in absorbing the heat of reaction and secondly ensure safe operation of the heterogeneously catalyzed gas phase partial oxidation of an organic compound by keeping the reaction gas mixture outside the explosion range. In heterogeneously catalyzed gas phase partial oxidations of unsaturated organic compound, saturated hydrocarbons, i.e. combustible gases, are frequently also used as inert diluent gases.

In many cases, the heterogeneously catalyzed gas phase partial oxidation is not carried out in one reactor, but rather in two or more reactors connected in series (which may also merge seamlessly into one another in a combined casing). Both such series connections of oxidation reactors and individual reactors used in themselves shall be encompassed in this document under the term "oxidation reactor system". In the same manner, both a single apparatus which is used in itself for the removal of the at least one target compound from the product gas (mixture) of the partial oxidation and the series connection of such removal apparatus shall be referred to in this document as removal system. Neither the term oxidation reactor system nor the term removal system includes parallel operation.

Normally, a series connection composed of an oxidation reactor system (a reactor line) and a removal system (a workup line) then forms a production system (a production line) for the preparation of organic target compounds by heterogeneously catalyzed gas phase partial oxidation of at least one organic precursor compound with molecular oxygen. In the oxidation reactor system, the starting reaction gas mixture comprising at least one organic precursor compound, molecular oxygen and at least one inert diluent gas is conducted through at least one fixed catalyst bed at elevated temperature, and, in the removal system, the target compound is removed from the product gas (mixture) of the partial oxidation as the crude target product stream. When the removal system consists of a plurality of removal apparatuses connected in series, the product gas (mixture) of the partial oxidation forms the stream fed to the first removal apparatus of the removal system. The stream leaving the last removal apparatus of the removal system is the crude target product stream and the streams conducted within the removal system from upstream to downstream removal apparatuses form, as already stated, in this document "subsequent streams".

An oxidation reactor system consisting of more than one reactor is employed especially when the partial oxidation proceeds in successive steps. In these cases, it is frequently appropriate to adjust both the catalyst and the other reaction conditions in an optimizing manner to the particular reaction step, and to carry out the particular reaction step in a dedicated reactor zone or in a dedicated reactor. In a typical manner, such a multistage oxidation reactor system is used, for example, in the partial oxidation of propylene to acrylic acid. In the first reaction zone (in the first reactor, in the first reaction stage), the propylene is oxidized to acrolein, and, in the second reaction zone (in the second reactor, in the second reaction stage), the acrolein is oxidized to acrylic acid. In a corresponding manner, the methacrylic acid preparation, usually starting from isobutene, is generally also carried out in two reaction zones connected in series (in two reactors connected in series).

It is of course possible in an oxidation reactor system for the reaction gas mixture to be cooled and/or supplemented with molecular oxygen (for example by addition of air) and/or inert gas between two oxidation reactors connected in series. However, both of the aforementioned partial oxidations may also be carried out in single reactor systems, in which the two reaction zones connected in series and charged with different catalysts are encased in a single reactor which then usually has two temperature zones. When suitable catalysts are used, both of the aforementioned partial oxidations may also be carried out in a single reactor having only one temperature zone.

A series connection of a plurality of oxidation reactors is in many cases also employed in order to, for reasons of heat removal or for other reasons (cf. DE-A 199 02 562), spread the conversion between a plurality of reactors connected in series. Typically, heterogeneously catalyzed gas phase partial oxidations are carried out in tube bundle reactors, as described, for example, in the German application DE-A 10 2004 025 445.

The removal system for acrylic acid prepared by heterogeneously catalyzed partial oxidation of propane and/or propylene consists typically of a series connection of direct cooling, absorption, stripping, rectification(s) and, if appropriate, crystallization(s) (cf., for example, DE-A 103 36 386 and US-A 2004/0242826).

While it is comparatively simple in construction terms to provide removal apparatus for large production capacities, oxidation reactors meet limits here at an earlier stage. The cause of this is that heterogeneously catalyzed gas phase partial oxidations generally proceed with marked exothermicity. This leads to the task of sufficient heat removal no longer being controllable with increasing production size of a single reactor.

It is therefore known from Process Economics Program Report No. 6C, Acrylic Acids and Acrylic Esters, SRI International, Menlo Park Calif. 94025 (1987), page 1 to 40 to prepare acrylic acid by operating two reactor lines in parallel, of which each consists of a series connection of a one-stage reactor (propylene→acrolein) and of a two-stage reactor (acrolein→acrylic acid). This is also referred to as parallel operation of two tandem reactor arrangements. The product gas leaving the particular tandem reactor arrangement is then mixed with the product gas leaving the tandem reactor arrangement operated in parallel to give a mixture stream and this mixture stream is sub-sequentially conducted for the removal of the acrylic acid into only one removal line (workup line) common to both reactor lines. The aforementioned operating mode is also recommended by FIG. 6 of WO 01/96271, and DE-A 199 02 562 refers to it as a classical parallel connection and once again details it by way of example. The aforementioned SRI report was also part of the public opposition proceedings against the patents EP-B 700 714 and EP-B 700 893, and the opponent is attempting once again in US-A 2004/0242826 to file the classical parallel connection as a patent.

A disadvantage of the classical parallel connection, in which the catalyst charges of both reactor lines are both taken into operation in parallel and subsequently operated in parallel, is, however, that both the target product selectivity and the by-product selectivity in both reactor lines develop synchronously over their operating time.

Typically, such operating times of catalyst charges for heterogeneously catalyzed gas phase partial oxidations, depending on the catalyst system and partial oxidation, are from several months to several years. A target and by-product selectivity which develops synchronously over such operating periods of partial oxidation catalyst charges operated in parallel in the classical manner is disadvantageous in that neither the target product selectivity nor the by-product selectivities of the catalyst charges generally remain constant over the operating times mentioned. Instead, in many cases, the target product selectivity decreases over the operating time and the by-product selectivity increases. However, cases are also known in which the target product selectivity increases over the operating time of the catalyst charge and the by-product selectivity decreases. The aforementioned also applies when, as recommended in EP-A 990 636 and EP-A 1 106 598, an attempt is made to counteract the aging of the catalyst bed by, in the course of the operating time of the catalyst bed, under otherwise substantially uniform operating conditions, the operating temperature of the catalyst bed is increased gradually (which generally simultaneously causes an acceleration of the aging process) and/or when, as recommended in EP-A 614 872 and in DE-A 103 50 822, the catalyst charge is regenerated from time to time. Neither the partial catalyst change recommended in DE-A 102 32 748 nor the variation in the working pressure recommended in the German application DE-A 10 2004 025 445 is capable of remedying the above-mentioned problem of change in selectivity.

However, such an accompanying change in selectivity over the operating time forms a burden for the performance of the removal line required over time. When the byproduct selectivity is small, it can be retained in an uncomplicated manner in order to achieve the separation task in a satisfactory manner. When the by-product selectivity is large, the removal line has to be configured in a complicated manner in order to satisfactorily achieve the separation task which is then more difficult.

When the by-product selectivity varies over the operating time, the configuration of the removal line in the case of classical parallel operation then has to be directed to the highest by-product selectivity achieved during the overall operating time in order to be able to prepare the crude target product with the required purity over the entire operating time (until the catalyst charge is changed). In other words, the removal line has to be configured with a very high degree of complexity. The latter is an economic burden. It was therefore an object of the invention, for example, to provide a process, as described at the outset, for the preparation of at least one organic target compound by heterogeneously catalyzed gas phase partial oxidation of at least one organic precursor compound with molecular oxygen, which is less demanding in economic terms.

Accordingly, a process has been found for preparing at least one organic target compound by a) heterogeneously catalyzed gas phase partial oxidation of at least one organic precursor compound with molecular oxygen in at least two oxidation reactor systems which comprise catalyst charges and are operated in parallel to obtain at least two product gas (mixture) streams each comprising the target compound and each stemming from one of the at least two oxidation reactor systems and b) subsequent removal of the at least one target compound from the at least two product gas (mixture) streams to obtain at least one crude target product stream, in which c) before the removal, mixing together at least two of the at least two product gas (mixture) streams, or, in the course of the removal, mixing together at least two of any target product-comprising subsequent streams obtained on the route from the at least two product gas (mixture) streams to the at least one crude target product stream, and/or, after the removal from the at least two product gas (mixture) streams, mixing together any crude target product streams obtained in the course of the removal, to form a mixture stream, wherein at least one of the catalyst charges of the at least two oxidation reactor systems operated in parallel comprises a portion of catalyst (based on the catalyst charge, preferably at least 20% by weight, or at least 40% by weight, better at least 60% by weight, even better at least 80% by weight and at best at least the entire amount of the catalyst charge) over which the heterogeneously catalyzed gas phase partial oxidation has already been carried out longer than over all portions of catalyst of the at least one other catalyst charge.

In general, the number of oxidation reactor systems (these are the oxidation reactor systems in which the target compounds comprised in the mixture stream were formed) operated in parallel in the inventive manner in the process according to the invention will be two. However, this number may also be three, four, five or more. In addition, the oxidation reactor systems operated in parallel in the inventive manner in the process according to the invention will preferably be of identical reactor design. This means that they are preferably designed for equal production capacities of target product and in the same way. In the case of tube bundle reactors, this means that their catalyst tubes are generally of the same type and substantially the same number. The same applies to the principle of heat removal employed.

In principle, the oxidation reactor systems operated in parallel in the inventive manner in the process according to the invention may, however, also be different from one another. This is true in the case of tube bundle reactors, for example, both with regard to different catalyst tube properties (for example length, wall thickness, internal diameter, length, material) and with regard to different catalyst tube number. The oxidation reactor systems operated in parallel in accordance with the invention may also be of entirely different type. In general, the charge gas mixture of oxidation reactor systems operated in parallel in accordance with the invention will be identical. In other words, both the composition of the charge gas mixture and the hourly space velocities on the catalyst charges in the oxidation reactor systems of charge gas mixture will normally be the same in oxidation reactor systems operated in parallel in accordance with the invention.

In other words, it is possible, for example, first to obtain an overall stream of starting reaction gas mixture comprising the at least one organic precursor compound and to feed this subsequently through a distributor system to the at least two oxidation reactor systems operated in parallel (for example those for the partial oxidative preparation of acrylic acid).

While, in the above variant, only one air compressor (from which the secondary air which may be required is also withdrawn) and only one cycle gas compressor (preferably in accordance with the invention, only one cycle gas remains in the target product removal) are of course employed for the at least two oxidation reactor systems operated in parallel (preference is given to radial compressors according to DE-A 10353014; the compression of the cycle gas and of the air may be carried out in two separate compressors which are driven with two separate motors, or in two compressors which are driven with one motor, or in a single compressor driven with one motor), it is appropriate in accordance with the invention only to use one air compressor (from which the secondary air which may be required is also withdrawn) and only one cycle gas compressor even when the starting reaction gas mixture for each of the at least two oxidation reactor systems operated in parallel is blended spatially separately. In this case, the compressed gases will be stored, for example, in lines, fed therefrom to the particular static mixer, and blended there with the organic precursor compound under appropriate pressure to give the particular starting reaction gas mixture for the particular oxidation reactor system.

The entry of the individual gases into the line fed to the static mixer is appropriately frequently selected in such a way that the formation of explosive mixtures is prevented (in the case of a partial oxidation of propylene to, for example, acrolein and/or acrylic acid, this entry sequence might appropriately, for example, be first cycle gas and/or steam, then (crude) propene and then air). The individually generated starting reaction gas mixture is then fed to the oxidation reactor system assigned to it in each case of the at least two oxidation reactor systems operated in parallel.

In this document, the hourly space velocity of a catalyst bed catalyzing a reaction step of (starting) reaction gas mixture is understood to be the amount of (starting) reaction gas mixture in standard liters (=l (STP); the volume in liters which would be taken up by the corresponding amount of (starting) reaction gas mixture under standard conditions, i.e. at 25° C. and 1 bar) which is conducted per hour through one liter of catalyst bed. The hourly space velocity may also be based only on one constituent of the (starting) reaction gas mixture. In that case, it is the amount of this constituent in l (STP)/l·h which is conducted through one liter of the catalyst bed per hour. Pure inert material beds are not included in the catalyst bed.

The same applies to the working pressure and the working temperature in the oxidation reactor systems operated in parallel in accordance with the invention. The aforementioned parameters (composition of the charge gas mixture (for the same precursor compound and same target product), hourly space velocity on the catalyst charges of organic precursor compound or reaction gas mixture, working temperature, working pressure) may of course also, individually or in groups, be different from one another. In terms of its type (i.e. in its chemical and physical properties), the catalyst charge in the oxidation reactor systems operated in parallel in accordance with the invention will frequently be identical (disregarding differences caused by different operating times).

However, the oxidation reactor systems operated in parallel in accordance with the invention may also be charged with catalysts of different type.

It is essential to the invention that at least one of the relevant catalyst charges (these are the catalyst charges over which the target compounds comprised in the mixture stream have been formed) of the at least two oxidation reactor systems operated in parallel in accordance with the invention comprises at least one portion of catalyst over which the heterogeneously catalyzed gas phase partial oxidation has already been carried out for a longer period than over all portions of catalyst of the at least one other catalyst charge.

This inventive feature can be realized in a simple manner, for example, by initially taking into operation at least two oxidation reactor systems, which have, for example, an identical charge of catalyst, in parallel with, for example, identical charge gas mixture and under identical other reaction conditions, and operating them over a prolonged period. When the selectivity of target product formation falls with increasing operating time as a result of aging of the catalyst charge (for example to a value which would be prohibitive for the target product removal with regard to the desired purity of the crude target product), the inventive operating mode can be achieved, for example, in a simple manner by undertaking a partial catalyst change, for example according to DE-A 102 32 748, only in one of the at least two oxidation reactor systems operated in parallel. Thereafter, the parallel operation can be continued in the inventive manner. The target product removal is burdened only with a by-product mixed selectivity and is still capable of producing the crude target product with the desired purity.

In this way, the lifetime of such catalyst charge, over which no partial catalyst change has been undertaken, can be significantly prolonged without additional cost and inconvenience. It is of course possible, instead of replacing just a portion of a catalyst charge with fresh catalyst, also to replace the entire amount of this catalyst charge with fresh catalyst and subsequently to proceed further in accordance with the invention.

Advantageously in accordance with the invention, the product gas (mixture) streams of at least two oxidation reactor systems operated in parallel in the inventive manner will be combined to give a mixture stream before their entry into the first apparatus of the target product removal. Of course, the target product removal in the process according to the invention may, though, initially also be performed in parallel in, for example, a manner corresponding to the at least two oxidation reactor systems operated in parallel. This may be advantageous when the target product removal consists of a plurality of separation apparatuses connected in series, of which only one is particularly capital-intensive or critical in another way. It may then be appropriate in accordance with the invention to design the target product removal in parallel up to the particularly cost-intensive (critical) removal apparatus, and only then to combine the corresponding target product-comprising subsequent streams to give a mixture stream in order to feed this mixture stream subsequently to only one critical separating apparatus. Beyond this separating apparatus, the parallel design of any further target product removal is preferably ended in an appropriate manner.

On the other hand, the target product removal in the process according to the invention may also be designed in parallel up to the occurrence of the crude target product streams. In this case, crude target product streams are normally obtained in accordance with the invention which have different impurity contents. While one of the two may oversatisfy the impurity specification required by the market, the other crude target product stream possibly does not satisfy it. When the two crude target product streams are blended, a crude target product stream may be obtained which is on-spec in its entirety.

When three oxidation reactor systems are operated in parallel in the inventive manner, it is possible, for example, instead of combining the product gas (mixture) streams of all three systems, and working up the resulting mixture, also to combine only two of the three product gas (mixture) streams and to work them up in a mixture. The workup of the third product gas stream may be effected separately and the two crude target product streams obtained may subsequently be mixed, etc.

A different operating time of the catalyst charges of at least two oxidation reactor systems operated in parallel can also be established (for example also by appropriate time-offset startup of the fresh catalyst charges) by operating the catalyst charges, constantly or over a scheduled period, at different temperatures and/or different hourly space velocities of precursor compound. In other words, the measure relevant in accordance with the invention for the operating time of a catalyst charge is the time in the chronometric sense only in the case of identical operating conditions and identical catalyst charge type. Otherwise, it is the amount of target product already produced over the catalyst charge. The more target product has already been produced over the catalyst charge, the greater is its perceived age. In the case of a multistage heterogeneously catalyzed gas phase partial oxidation proceeding via at least one intermediate, a measure which applies for the operating time of the catalyst charge over which the intermediate is formed is correspondingly the total amount of intermediate already produced over this charge.

In the case of a two-stage preparation of acrylic acid from propylene, this would be, for the catalyst charge of the first reaction stage, for example, the total amount of acrolein already formed over this catalyst charge.

In the case of a two-stage preparation of methacrylic acid from isobutene, this would be, for the catalyst charge of the first reaction stage, for example, the total amount of methacrolein already formed over this catalyst charge. For the catalyst charges of the second reaction stage, the corresponding measure for the operating period would be the amount of acrylic acid or methacrylic acid already formed over the particular catalyst charge.

In other words, in the case of a multistage heterogeneously catalyzed gas phase partial oxidation carried out in at least two oxidation reactor systems operated in parallel, use is also made of the inventive procedure already by one who, after a certain operating time, replaces at least a portion of the catalyst charge (preferably at least 20% by weight, better at least 40% by weight, even better at least 60% by weight, or at least 80% by weight and at best 100% by weight based on the catalyst charge) with fresh catalyst only in a single oxidation stage of the relevant oxidation reactor system and subsequently proceeds further in accordance with the invention. In the case of a two-stage preparation of acrylic acid from propylene, this partial or full catalyst change may be undertaken, for example, only in the "propylene→acrolein" reaction stage in one of the relevant at least two oxidation reactor systems operated in parallel. It may of course also be undertaken in both reaction stages in one of the relevant at least two oxidation reactor systems operated in parallel. According to the invention, it is also conceivable that the partial and full catalyst change is undertaken in one of the relevant at least two oxidation reactor systems operated in parallel only in the first reaction stage and in the other of the relevant at least two oxidation reactor systems operated in parallel only in the second reaction stage.

When the selectivity of target product formation grows with increasing operating time of the catalyst charge and only its activity decreases with increasing operating time, it is possible to proceed in a corresponding manner.

Thus, the relevant at least two oxidation reactor systems operated in parallel can be operated with fresh catalyst charges in each case initially for a certain time under identical conditions and the mixture stream of the at least two product gas streams can be fed to a single removal system. The latter can be designed in such a way that it initially generates a crude target product stream with comparatively low purity on the basis of the initially high selectivity of by-product formation. For example, this crude target product stream may be crude acrylic acid which can be used further only for the preparation of alkyl esters (for example butyl, methyl, ethyl or 2-ethylhexyl esters). When a partial or full catalyst change is subsequently carried out in the inventive manner, an average target product selectivity in the mixture of the relevant at least two product gas streams, which leads in the same removal system to a crude target product stream with comparatively increased purity, will be achieved in the further course of inventive operation. For example, this crude target product stream may then be "glacial" acrylic acid which is suitable for preparing superabsorbent polyacrylic acids or their sodium salts.

It is of course also possible to store initially produced, less on-spec crude acrylic acid in a large tank and mix it with subsequent crude acrylic acid which over-fulfills the desired specification to give an on-spec total amount of crude acrylic acid.

However, use is also made of the process according to the invention when the relevant at least two oxidation reactor systems operated in parallel are charged with catalyst charges of which one forms the target compound with selectivity increasing over the operating time and the other the target compound with selectivity decreasing over the operating time. In this way, different amounts of target product have been formed in the at least two catalyst charges even after a short chronometric operating time and thus "different" operating times of the two catalyst charges are thus achieved in the inventive sense.

In the case of an inventive multistage heterogeneously catalyzed gas phase partial oxidation of at least one organic precursor compound, it is advantageous in accordance with the invention actually to combine the product gas streams of the relevant at least two first reaction stages operated in parallel to give a mixture stream (as is already practiced in the classical parallel connection of DE-A 199 02 562), and to use this, if appropriate supplemented by inert gas and/or molecular oxygen, to charge and operate the at least two subsequent reaction stages in parallel.

In principle, the process according to the invention is suitable for all heterogeneously catalyzed gas phase partial oxidations listed specifically at the outset of this document. These include in particular also the heterogeneously catalyzed gas phase partial oxidation of propane to acrylic acid described by way of example in the documents WO 01/96270, DE-A 103 16 465, DE-A 102 45 585 and DE-A 102 46 119. The aforementioned documents, just like US-A 2004/0242826 and DE-A 103 36 386, are also to be viewed as an integral part of this document. The inventive procedure is also suitable in principle for heterogeneously catalyzed partial oxidations carried out in a fluidized catalyst bed.

Advantageously in accordance with the invention, the inventive heterogeneously catalyzed gas phase partial oxidation of at least one organic precursor compound with molecular oxygen can also be carried out in accordance with the invention in at least two tube bundle reactors operated in parallel, of which one is operated in cocurrent to the reaction gas mixture viewed over the reactor and the other in countercurrent to the reaction gas mixture viewed over the reactor. The latter generally leads to accelerated aging of the catalyst charge when, apart from the direction, operation is effected under otherwise identical conditions.

Advantageously in accordance with the invention, at least one of the relevant catalyst charges of the at least two oxidation reactor systems operated in parallel in the process according to the invention should comprise at least one portion of catalyst (in the case of a multistage partial oxidation, for example, the entire amount of catalyst of the first and/or the second reaction stage, or portions of the catalyst charges of the first and/or second reaction stage) over which the heterogeneously catalyzed gas partial oxidation has already been carried out for at least 30 calendar days, preferably at least 60 calendar days or at least 90 calendar days and more preferably at least 120 or at least 150 calendar days, and most preferably at least 180 calendar days or at least 210 or 240 calendar days, longer than over all portions of catalyst of the other catalyst charge.

However, processes of the invention are also those in which the aforementioned operating time difference is at least 270, or at least 300, or at least 330, or at least 360, or at least 400, or at least 450, or at least 500, or at least 550, or at least 600, or at least 700, or at least 800, or at least 900, or at least 1000 days, or at least 2000 days, or at least 3000 days or more. In general, it will not be more than three years or 1000 days, usually not more than two years or 750 days.

Expressed in the total amount of target product or intermediate already produced additionally over this at least one portion of catalyst, the aforementioned operating time different may be at least $10^6$ kg, or at least $2 \cdot 10^6$ kg, or at least $3 \cdot 10^6$ kg, or at least $4 \cdot 10^6$ kg, or at least $5 \cdot 10^6$ kg, or at least $6 \cdot 10^6$ kg, or at least $7 \cdot 10^6$ kg, or at least $8 \cdot 10^6$ kg, or at least $9 \cdot 10^6$ kg or at least $10^7$ kg, or at least $1.5 \cdot 10^7$ kg, or at least $2 \cdot 10^7$ kg, or at least $3 \cdot$ or $4 \cdot 10^7$ kg, or at least $5 \cdot 10^7$ kg, or at least $6 \cdot 10^7$ kg, or at least $7 \cdot 10^7$ kg, or at least $8 \cdot 10^7$ kg, or at least $10^8$ kg, or at least $2 \cdot 10^8$ kg, or at least $3 \cdot 10^8$ kg, or at least $4 \cdot 10^8$ kg. Normally, the aforementioned operating time difference will not be more than $10^9$ kg, usually not more than $0.5 \cdot 10^9$ kg and frequently not more than $10^8$ kg.

It is significant in accordance with the invention that even small changes in the selectivity of by-product formation can make it significantly more complicated to obtain on-spec crude target product. A typical example is propionic acid as a by-product of acrylic acid. In order to be salable on the market, acrylic acid should not comprise more than, for example, 800 ppm by weight of propionic acid (depending on the end use). Similar limiting values apply in the case of acrylic acid, for example, for formaldehyde and acetic acid as by-product impurities. In many cases, the selectivity of target product formation in heterogeneously catalyzed gas phase partial oxidations changes within the first three months after startup of the catalyst charge by at least 0.1 or 0.2 mol %, or by at least 0.3 or 0.5 mol %, or by at least 1 mol % or by at least 1.5 mol %, or by at least 2 mol %, in some cases even by at least 3 or at least 4 or at least 7 mol %. The overall selectivity of secondary component formation changes generally within the same period correspondingly in many cases by likewise from at least 0.1 to 7 mol % and more.

Accordingly, in the process according to the invention, the difference of the relevant at least two catalyst charges operated in parallel in the selectivity of target product formation (e.g. acrylic acid formation) may, for example, be up to 7 mol % or more (for example 0.1, or 0.2, or from 0.3 to 7 mol %) and the difference in the overall selectivity of secondary component formation may likewise be up to 7 mol % or more (for example 0.1, or 0.2, or from 0.3 to 7 mol %).

However, the inventive procedure is particularly suitable for the heterogeneously catalyzed fixed bed gas phase partial oxidation, carried out preferably in a tube bundle reactor in one stage, of propene to acrolein and/or acrylic acid, and for the first and second stage of a heterogeneously catalyzed fixed bed gas phase partial oxidation, carried out in tube bundle reactors in two stages, of propene to acrolein and of acrolein to acrylic acid, as described, for example, in the documents EP-A 700 893, EP-A 700 714, DE-A 199 10 508, DE-A 199 10 506, DE-A 103 51 269, DE-A 103 50 812, DE-A 103 50 822, EP-A 11 59 247, DE-A 103 13 208, DE-A 10 2004 021

764, DE-A 199 48 248, EP-A 990 636, EP-A 11 06 598, DE-A 30 02 829 and DE-A 102 32 482.

The process according to the invention is suitable for a heterogeneously catalyzed gas phase fixed bed partial oxidation of propene to acrolein especially when the catalysts used are those whose active composition is a multielement oxide which comprises the elements molybdenum and/or tungsten, and also at least one of the elements bismuth, tellurium, antimony, tin and copper, or is a multimetal oxide comprising the elements Mo, Bi and Fe. Multimetal oxide compositions of the aforementioned type which comprise Mo, Bi and Fe and are particularly suitable in accordance with the invention are in particular the multimetal oxide compositions comprising Mo, Bi and Fe which are disclosed in DE-A 10 34 4149 and in DE-A 10 34 4264. These are in particular also the multimetal oxide active compositions of the general formula I of DE-A 19 95 5176, the multimetal oxide active compositions of the general formula I of DE-A 19 94 8523, the multimetal oxide active compositions of the general formulae I, II and III of DE-A 10 10 1695, the multimetal oxide active compositions of the general formulae I, II and III of DE-A 19 94 8248 and the multimetal oxide active compositions of the general formulae I, II and III of DE-A 19 95 5168 and also the multimetal oxide active compositions specified in EP-A 700 714.

An application of the process according to the invention is also suitable when the catalysts used for the at least two fixed catalyst beds to be used in accordance with the invention, in the case of the partial oxidation of propene to acrolein, are the multimetal oxide catalysts comprising Mo, Bi and Fe which are disclosed in the documents DE-A 10 04 6957, DE-A 10 06 3162, DE-C 33 38 380, DE-A 19 90 2562, EP-A 15 565, DE-C 23 80 765, EP-A 807 465, EP-A 279 374, DE-A 33 00 044, EP-A 575 897, US-A 4 438 217, DE-A 19 85 5913, WO 98/24746, DE-A 19 746 210 (those of the general formula II), JP-A 91/294 239, EP-A 293 224 and EP-A 700 714. This applies in particular to the exemplary embodiments in these documents, and among these particular preference is given to those of EP-A 15565, EP-A 575 897, DE-A 19 74 6210 and DE-A 19 85 5913. Particular emphasis is given in this context to a catalyst according to example 1c from EP-A 15 565 and also to a catalyst to be prepared in a corresponding manner but whose active composition has the composition $Mo_{12}Ni_{6.5}Zn_2Fe_2Bi_1P_{0.0065}K_{0.06}Ox \cdot 10\, SiO_2$. Emphasis is also given to the example having the serial number 3 from DE-A 19855913 (stoichiometry: $Mo_{12}CO_7Fe_3Bi_{0.6}K_{0.08}Si_{1.6}Ox$) as an unsupported hollow cylinder catalyst of geometry 5 mm×3 mm×2 mm or 5 mm×2 mm×2 mm (each external diameter×height×internal diameter) and also to the unsupported multimetal oxide 11 catalyst according to example 1 of DE-A 19 74 6210. Mention should also be made of the multimetal oxide catalysts of U.S. Pat. No. 4,438,217. The latter is true in particular when these have a hollow cylinder geometry of the dimensions 5.5 mm×3 mm×3.5 mm, or 5 mm×2 mm×2 mm, or 5 mm×3 mm×2 mm, or 6 mm×3 mm×3 mm, or 7 mm×3 mm×4 mm (each external diameter×height×internal diameter). Likewise suitable in the context of the present invention are the multimetal oxide catalysts and geometries of DE-A 10 10 1695 or WO 02/062737.

Also very suitable in the context of the present invention are example 1 of DE-A 10046957 (stoichiometry: $[Bi_2W_2O_9 \cdot 2WO_3]_{0.5} \cdot [Mo_{12}Co_{5.6}Fe_{2.94}Si_{1.59}K_{0.08}O_x]_1$) as an unsupported hollow cylinder (ring) catalyst of geometry 5 mm×3 mm×2 mm or 5 mm×2 mm×2 mm (each external diameter×length×internal diameter), and also the coated catalysts 1, 2 and 3 of DE-A 10063162 (stoichiometry: $Mo_{12}Bi_{1.0}Fe_3Co_7Si_{1.6}K_{0.08}$), except as annular coated catalysts of appropriate coating thickness and applied to support rings of geometry 5 mm×3 mm×1.5 mm or 7 mm×3 mm×1.5 mm (each external diameter×length×internal diameter).

A multitude of multimetal oxide active compositions particularly suitable for the catalysts of a propene partial oxidation to acrolein in the context of the present invention can be encompassed by the general formula I

$$Mo_{12}Bi_aFe_bX^1_cX^2_dX^3_eX^4_fO_n \qquad (I)$$

in which the variables are each defined as follows:
$X^1$=nickel and/or cobalt,
$X^2$=thallium, an alkali metal and/or an alkaline earth metal,
$X^3$=zinc, phosphorus, arsenic, boron, antimony, tin, cerium, lead and/or tungsten,
$X^4$=silicon, aluminum, titanium and/or zirconium,
a=from 0.5 to 5,
b=from 0.01 to 5, preferably from 2 to 4,
c=from 0 to 10, preferably from 3 to 10,
d=from 0 to 2, preferably from 0.02 to 2,
e=from 0 to 8, preferably from 0 to 5,
f=from 0 to 10 and
n=a number which is determined by the valency and frequency of the elements in I other than oxygen.

They are obtainable in a manner known per se (see, for example, DE-A 4023239) and are customarily shaped undiluted to give spheres, rings or cylinders or else used in the form of coated catalysts, i.e. preshaped inert support bodies coated with the active composition. It will be appreciated that they may also be used as catalysts in powder form.

In principle, active compositions of the general formula I can be prepared in a simple manner by obtaining a very intimate, preferably finely divided dry mixture having a composition corresponding to their stoichiometry from suitable sources of their elemental constituents and calcining it at temperatures of from 350 to 650° C. The calcination may be effected either under inert gas or under an oxidative atmosphere, for example air (mixture of inert gas and oxygen) and also under a reducing atmosphere (for example mixture of inert gas, $NH_3$, CO and/or $H_2$). The calcination time can be from a few minutes to a few hours and typically decreases with temperature. Useful sources for the elemental constituents of the multimetal oxide active compositions I are those compounds which are already oxides and/or those compounds which can be converted to oxides by heating, at least in the presence of oxygen.

In addition to the oxides, such useful starting compounds include in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate which decompose and/or can be decomposed on later calcining at the latest to give compounds which are released in gaseous form can be additionally incorporated into the intimate dry mixture).

The starting compounds for preparing multimetal oxide active compositions I can be intimately mixed in dry or in wet form. When they are mixed in dry form, the starting compounds are advantageously used as finely divided powders and subjected to calcining after mixing and optional compaction. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures from the spray tower of from 100 to 150° C.

Typically, the multimetal oxide active compositions of the general formula I are used in the fixed catalyst bed not in powder form, but rather shaped into certain catalyst geometries, and the shaping may be effected before or after the final calcination. For example, unsupported catalysts can be prepared from the powder form of the active composition or its uncalcined and/or partially calcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst can also have spherical geometry, and the spherical diameter may be from 2 to 10 mm.

A particularly advantageous hollow cylinder geometry is 5 mm×3 mm×2 mm (external diameter×length×internal diameter), in particular in the case of unsupported catalysts.

It will be appreciated that the pulverulent active composition or its pulverulent precursor composition which is yet to be calcined and/or partially calcined may also be shaped by applying to preshaped inert catalyst supports. The coating of the support bodies to produce the coated catalysts is generally performed in a suitable rotatable vessel, as disclosed, for example, by DE-A 2909671, EP-A 293859 or EP-A 714700. To coat the support bodies, the powder composition to be applied is appropriate moistened and dried again after application, for example by means of hot air. The coating thickness of the powder composition applied to the support body is advantageously selected within the range from 10 to 1000 μm, preferably within the range from 50 to 500 μm and more preferably within the range from 150 to 250 μm. Alternatively, the powder composition to be applied may also be applied to the support bodies directly from a suspension or solution thereof (for example in water).

Useful support materials are customary porous or nonporous aluminum oxides, silicon dioxide, thorium dioxide, zirconium dioxide, silicon carbide or silicates such as magnesium silicate or aluminum silicate. They generally behave substantially inertly with regard to the target reaction on which the process according to the invention in the first reaction stage is based. The support bodies may have a regular or irregular shape, although preference is given to regularly shaped support bodies having distinct surface roughness, for example spheres or hollow cylinders. It is suitable to use substantially nonporous, surface-roughened spherical supports made of steatite (e.g. Steatite C220 from CeramTec) whose diameter is from 1 to 8 mm, preferably from 4 to 5 mm. However, suitable support bodies also include cylinders whose length is from 2 to 10 mm (e.g. 8 mm) and whose external diameter is from 4 to 10 mm (e.g. 6 mm). In the case of rings which are suitable in accordance with the invention as support bodies, the wall thickness is also typically from 1 to 4 mm. Annular support bodies to be used with preference in accordance with the invention have a length of from 2 to 6 mm, an external diameter of from 4 to 8 mm and a wall thickness of from 1 to 2 mm. Also suitable in accordance with the invention are in particular rings of the geometry 7 mm×3 mm×4 mm or 5 mm×3 mm×2 mm (external diameter×length×internal diameter). It will be appreciated that the fineness of the catalytically active oxide compositions to be applied to the surface of the support body is adapted to the desired coating thickness (cf. EP-A 714 700).

Multimetal oxide active compositions which are particularly suitable for the catalysts of the fixed catalyst bed of a propene partial oxidation to acrolein in the context of the present invention are also compositions of the general formula II

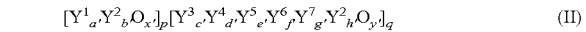

$$[Y^1_a Y^2_b O_{x'}]_p [Y^3_c Y^4_d Y^5_e Y^6_f Y^7_g Y^2_h O_{y'}]_q \quad (II)$$

in which the variables are each defined as follows:
$Y^1$=only bismuth or bismuth and at least one of the elements tellurium, antimony, tin and copper,
$Y^2$=molybdenum or molybdenum and tungsten,
$Y^3$=an alkali metal, thallium and/or samarium,
$Y^4$=an alkaline earth metal, nickel, cobalt, copper, manganese, zinc, tin, cadmium and/or mercury,
$Y^5$=iron or iron and at least one of the elements chromium and cerium,
$Y^6$=phosphorus, arsenic, boron and/or antimony,
$Y^7$=a rare earth metal, titanium, zirconium, niobium, tantalum, rhenium, ruthenium, rhodium, silver, gold, aluminum, gallium, indium, silicon, germanium, lead, thorium and/or uranium,
$a'$=from 0.01 to 8,
$b'$=from 0.1 to 30,
$c'$=from 0 to 4,
$d'$=from 0 to 20,
$e'$=from >0 to 20,
$f'$=from 0 to 6,
$g'$=from 0 to 15,
$h'$=from 8 to 16,
$x',y'$=numbers which are determined by the valency and frequency of the elements in II other than oxygen and
$p,q$=numbers whose p/q ratio is from 0.1 to 10,
comprising three-dimensional regions of the chemical composition $Y^1_a Y^2_b O_{x'}$ which are delimited from their local environment as a consequence of their different composition from their local environment, and whose maximum diameter (longest direct line passing through the center of the region and connecting two points on the surface (interface) of the region) is from 1 nm to 100 μm, frequently from 10 nm to 500 nm or from 1 μm to 50 or 25 μm.

Particularly advantageous multimetal oxide compositions III are those in which $Y^1$ is only bismuth.

Among these, preference is given in turn to those of the general formula III

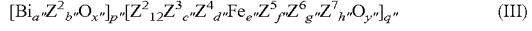

$$[Bi_{a''} Z^2_{b''} O_{x''}]_{p''} [Z^2_{12} Z^3_{c''} Z^4_{d''} Fe_{e''} Z^5_{f''} Z^6_{g''} Z^7_{h''} O_{y''}]_{q''} \quad (III)$$

in which the variables are each defined as follows:
$Z^2$=molybdenum or molybdenum and tungsten,
$Z^3$=nickel and/or cobalt,
$Z^4$=thallium, an alkali metal and/or an alkaline earth metal,
$Z^5$=phosphorus, arsenic, boron, antimony, tin, cerium and/or lead,
$Z^6$=silicon, aluminum, titanium and/or zirconium,
$Z^7$=copper, silver and/or gold,
$a''$=from 0.1 to 1,
$b''$=from 0.2 to 2,
$c''$=from 3 to 10,
$d''$=from 0.02 to 2,
$e''$=from 0.01 to 5, preferably from 0.1 to 3,
$f''$=from 0 to 5,
$g''$=from 0 to 10,
$h''$=from 0 to 1,
$x'',y''$=numbers which are determined by the valency and frequency of the elements in III other than oxygen, p″,q″=numbers whose p″/q″ ratio is from 0.1 to 5, preferably from 0.5 to 2, and very particular preference is given to those compositions III in which $Z^2{}_{b''}$=(tungsten)$_{b''}$ and $Z^2{}_{12}$=(molybdenum)$_{12}$.

It is also advantageous when at least 25 mol % (preferably at least 50 mol % and more preferably at least 100 mol %) of the total proportion of $[Y^1{}_{a'}Y^2{}_{b'}O_{x'}]_p$ ($[Bi_{a''}Z^2{}_{b''}O_{x''}]_{p''}$) of the multimetal oxide compositions II (multimetal oxide compositions III) suitable in accordance with the invention in the multimetal oxide compositions II (multimetal oxide compositions III) suitable in accordance with the invention are in the form of three-dimensional regions of the chemical composition $Y^1{}_{a'}Y^2{}_{b'}O_{x'}$·[$Bi_{a''}Z^2{}_{b''}O_{x''}$] which are delimited from their local environment as a consequence of their different chemical composition from their local environment, and whose maximum diameter is in the range from 1 nm to 100 μm.

With regard to the shaping, the statements made for the multimetal oxide I catalysts apply to multimetal oxide II catalysts.

The preparation of multimetal oxide active compositions II is described, for example, in EP-A 575897 and also in DE-A 19855913, DE-A 10344149 and DE-A 10344264.

Suitable active compositions for catalysts of at least one fixed catalyst bed suitable for the partial oxidation of acrolein to acrylic acid in the context of the present invention are the multimetal oxides known for this reaction type which comprise the elements Mo and V.

Such multimetal oxide active compositions comprising Mo and V can be taken, for example, from U.S. Pat. No. 3,775,474, U.S. Pat. No. 3,954,855, U.S. Pat. No. 3,893,951, and U.S. Pat. No. 4,339,355, or EP-A 614872 or EP-A 1041062, or WO 03/055835, or WO 03/057653.

Especially suitable are also the multimetal oxide active compositions of DE-A 10 32 5487 and also of DE-A 10 325 488.

Also particularly suitable as active compositions for the fixed bed catalysts for the partial oxidation of acrolein to acrylic acid in the context of the present invention are the multimetal oxide compositions of EP-A 427508, DE-A 29 09 671, DE-C 31 51 805, DE-B 26 26 887, DE-A 43 02 991, EP-A 700 893, EP-A 714 700 and DE-A 19 73 6105. Particular preference is given in this context to the exemplary embodiments of EP-A 714 700 and of DE-A 19 73 6105.

A multitude of these multimetal oxide active compositions comprising the elements Mo and V can be encompassed by the general formula IV

$$Mo_{12}V_aX^1{}_bX^2{}_cX^3{}_dX^4{}_eX^5{}_fX^6{}_gO_n \quad (IV)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in IV other than oxygen.

Preferred embodiments among the active multimetal oxides IV in the context of the present invention are those which are encompassed by the following definitions of the variables of the general formula IV:
$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^6$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in IV other than oxygen.

However, multimetal oxides IV which are very particularly preferred in the context of the present invention are those of the general formula V

$$Mo_{12}V_{a'}Y^1{}_{b'}Y^2{}_{c'}Y^5{}_{f'}Y^6{}_{g'}O_{n'} \quad (V)$$

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in V other than oxygen.

Multimetal oxide active compositions (IV) are obtainable in a manner known per se, for example disclosed in DE-A 43 35 973 or in EP-A 714 700. In particular, suitable multimetal oxide active compositions comprising Mo and V in the context of the present invention for the partial oxidation of acrolein to acrylic acid are also the multimetal oxide active compositions of DE-A 10 261 186.

In principle, such multimetal oxide active compositions comprising Mo and V, especially those of the general formula IV, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions IV include those compounds which are already oxides and/or those compounds which can be converted to oxides by heating, at least in the presence of oxygen.

The starting compounds for preparing multimetal oxide compositions IV can be intimately mixed in dry or in wet form. When they are mixed in dry form, the starting compounds are advantageously used as finely divided powder and subjected to calcining after mixing and optional compaction. However, preference is given to intimate mixing in wet form. Customarily, the starting compounds are mixed with each other in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The multimetal oxide active compositions comprising Mo and V, especially those of the general formula IV, may be used for the process according to the invention of a partial oxidation of acrolein to acrylic acid either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst may also have spherical geometry, and the spherical diameter may be from 2 to 10 mm.

It will be appreciated that the pulverulent active composition or its pulverulent precursor composition which is yet to be calcined may also be shaped by applying to preshaped inert catalyst supports. The coating of the support bodies to produce the coated catalysts is generally performed in a suitable rotatable vessel, as disclosed, for example, by DE-A 2909671, EP-A 293859 or by EP-A 714700.

To coat the support bodies, the powder composition to be applied is appropriately moistened and dried again after application, for example by means of hot air. The coating thickness of the powder composition applied to the support body is advantageously selected within the range from 10 to 1000 µm, preferably within the range from 50 to 500 µm and more preferably within the range from 150 to 250 µm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders. It is suitable to use substantially nonporous, surface-roughened, spherical supports made of steatite whose diameter is from 1 to 10 mm (e.g. 8 mm), preferably from 4 to 5 mm. However, suitable support bodies also include cylinders whose length is from 2 to 10 mm and whose external diameter is from 4 to 10 mm. In the case of rings which are suitable in accordance with the invention as support bodies, the wall thickness is also typically from 1 to 4 mm. Annular support bodies to be used with preference in accordance with the invention have a length of from 3 to 6 mm, an external diameter of from 4 to 8 mm and a wall thickness of from 1 to 2 mm. Suitable support bodies according to the invention are also in particular rings of geometry 7 mm×3 mm×4 mm (external diameter×length× internal diameter). It will be appreciated that the fineness of the catalytically active oxide compositions to be applied to the surface of the support body is adapted to the desired coating thickness (cf. EP-A 714 700).

Advantageous multimetal oxide active compositions comprising Mo and V and which are to be used in the context of the present invention for an acrolein partial oxidation to acrylic acid are also compositions of the general formula VI $$[D]_p[E]_q \quad (VI)$$

in which the variables are each defined as follows:
$D=Mo_{12}V_{a''}Z^1_{b''}Z^2_{c''}Z^3_{d''}Z^4_{e''}Z^5_{f''}Z^6_{g''}O_{x'''}$,
$E=Z^7_{12}Cu_{h''}H_{i''}O_{y'''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta,
$a''$=from 1 to 8,
$b''$=from 0.2 to 5,
$c''$=from 0 to 23,
$d''$=from 0 to 50,
$e''$=from 0 to 2,
$f''$=from 0 to 5,
$g''$=from 0 to 50,
$h''$=from 4 to 30,
$i''$=from 0 to 20 and
$x'',y''$=numbers which are determined by the valency and frequency of the elements in VI other than oxygen and
p,q=numbers other than zero whose p/q ratio is from 160:1 to 1:1,
and which are obtainable by separately preforming a multimetal oxide composition E $$Z^7_{12}Cu_{h''}H_{i''}O_{y''} \quad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to those multimetal oxide active compositions VI in which the preformed solid starting composition 1 is incorporated into an aqueous starting composition 2 at a temperature of <70° C. A detailed description of the preparation of multimetal oxide composition III catalysts is comprised, for example, in EP-A 668104, DE-A 19736105 and DE-A 19528646.

With regard to the shaping, the statements made for the multimetal oxide active composition IV catalysts apply to multimetal oxide active composition VI catalysts.

Further multimetal oxide active compositions comprising Mo and V which are advantageous in the context described are also multielement oxide active compositions of the general formula VII $$[A]_p[B]_q[C]_r \quad (VII)$$

in which the variables are each defined as follows:
$A=Mo_{12}V_aX^1_bX^2_cX^3_dX^4_eX^5_fX^6_gO_x$,
$B=X^7_1Cu_hH_iO_y$,
$C=X^8_1Sb_jH_kO_z$,
$X^1$=W, Nb, Ta, Cr and/or Ce, preferably W, Nb and/or Cr,
$X^2$=Cu, Ni, Co, Fe, Mn and/or Zn, preferably Cu, Ni, Co and/or Fe, $X^3$=Sb and/or Bi, preferably Sb,
$X^4$=Li, Na, K, Rb, Cs and/or H, preferably Na and/or K,
$X^5$=Mg, Ca, Sr and/or Ba, preferably Ca, Sr and/or Ba,
$X^6$=Si, Al, Ti and/or Zr, preferably Si, Al and/or Ti,
$X^7$=Mo, W, V, Nb and/or Ta, preferably Mo and/or W,
$X^8$=Cu, Ni, Zn, Co, Fe, Cd, Mn, Mg, Ca, Sr and/or Ba, preferably Cu and/or Zn, more preferably Cu,
a=from 1 to 8, preferably from 2 to 6,
b=from 0.2 to 5, preferably from 0.5 to 2.5
c=from 0 to 23, preferably from 0 to 4,
d=from 0 to 50, preferably from 0 to 3,
e=from 0 to 2, preferably from 0 to 0.3,
f=from 0 to 5, preferably from 0 to 2,
g=from 0 to 50, preferably from 0 to 20,
h=from 0.3 to 2.5, preferably from 0.5 to 2, more preferably from 0.75 to 1.5,
i=from 0 to 2, preferably from 0 to 1,
j=from 0.1 to 50, preferably from 0.2 to 20, more preferably from 0.2 to 5,
k=from 0 to 50, preferably from 0 to 20, more preferably from 0 to 12,
x,y,z=numbers which are determined by the valency and frequency of the elements in A, B, C other than oxygen,
p, q=positive numbers
r=0 or a positive number, preferably a positive number, where the p/(q+r) ratio=from 20:1 to 1:20, preferably from 5:1 to 1:14 and
more preferably from 2:1 to 1:8 and, in the case that r is a positive number, the q/r ratio=from 20:1 to 1:20, preferably from 4:1 to 1:4,
more preferably from 2:1 to 1:2 and most preferably 1:1, which comprise the fraction $[A]_p$ in the form of three-dimensional regions (phases) A of the chemical composition

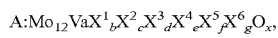
A:$Mo_{12}VaX^1_bX^2_cX^3_dX^4_eX^5_fX^6_gO_x$, the fraction $[B]_q$ in the form of three-dimensional regions (phases) B of the chemical composition

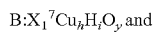
B:$X_1^7Cu_hH_iO_y$, and the fraction $[C]_r$ in the form of three-dimensional regions (phases) C of the chemical composition

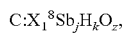
C:$X_1^8Sb_jH_kO_z$, where the regions A, B and, where present, C are distributed relative to each other as in a mixture of finely divided A, finely divided B and, where present, finely divided C, and where all variables are to be selected within the predefined ranges with the proviso that the molar fraction of the element Mo in the total amount of all elements in the multielement oxide active composition VII other than oxygen is from 20 mol % to 80 mol %, the molar ratio of Mo present in the catalytically active multielement oxide composition VII to V present in the catalytically active multielement oxide composition VII, Mo/V, is from 15:1 to 1:1, the corresponding molar Mo/Cu ratio is from 30:1 to 1:3 and the corresponding molar Mo/(total amount of W and Nb) ratio is from 80:1 to 1:4.

In the context of the present invention, preferred multielement oxide active compositions VII are those whose regions A have a composition within the following stoichiometric pattern of the general formula VIII:

$Mo_{12}V_aX^1_bX^2_cX^5_fX^6_gO_x$ (VIII)

where
$X^1$=W and/or Nb,
$X^2$=Cu and/or Ni,
$X^5$=Ca and/or Sr,
$X^6$=Si and/or Al, a=from 2 to 6,
b=from 1 to 2,
c=from 1 to 3,
f=from 0 to 0.75,
g=from 0 to 10, and
x=a number which is determined by the valency and frequency of the elements in (VIII) other than oxygen.

The term "phase" used in connection with the multielement oxide active compositions VIII means three-dimensional regions whose chemical composition is different to that of their environment. The phases are not necessarily x-ray-homogeneous. In general, phase A forms a continuous phase in which particles of phase B and, where present, C are dispersed.

The finely divided phases B and, where present, C advantageously consist of particles whose largest diameter, i.e. longest line passing through the center of the particles and connecting two points on the surface of the particles, is up to 300 μm, preferably from 0.1 to 200 μm, more preferably from 0.5 to 50 μm and most preferably from 1 to 30 μm. However, particles having a largest diameter of from 10 to 80 μm or from 75 to 125 μm are also suitable.

In principle, the phases A, B and, where present, C may be in amorphous and/or crystalline form in the multielement oxide active compositions VII.

The intimate dry mixtures on which the multielement oxide active compositions of the general formula VII are based and which are subsequently to be treated thermally to convert them to active compositions may be obtained, for example, as described in the documents WO 02/24327, DE-A 4405514, DE-A 4440891, DE-A 19528646, DE-A 19740493, EP-A 756894, DE-A 19815280, DE-A 19815278, EP-A 774297, DE-A 19815281, EP-A 668104 and DE-A 19736105.

The basic principle of preparing intimate dry mixtures whose thermal treatment leads to multielement oxide active compositions of the general formula VII is to preform, in finely divided form, separately or combined together, at least one multielement oxide composition B ($X_1^7Cu_hH_iO_y$) as the starting composition 1 and, where appropriate, one or more multielement oxide compositions C($X_1^8Sb_jH_kO_z$) as the starting composition 2, and subsequently to intimately contact, in the desired ratio (corresponding to the general formula VII), the starting compositions 1 and, where appropriate, 2 with a mixture which comprises sources of the elemental constituents of the multielement oxide composition A

$Mo_{12}V_aX^1_bX^2_cX^3_dX^4_eX^5_fX^6_gO_x$ (A)

in a composition corresponding to the stoichiometry A, and optionally to dry the resulting intimate mixture.

The intimate contacting of the constituents of the starting compositions 1 and, where appropriate, 2 with the mixture comprising the sources of the elemental constituents of the multimetal oxide composition A (starting composition 3) may be effected either in dry or in wet form. In the latter case, care has to be taken merely that the preformed phases (crystallites) B and, where appropriate, C do not go into solution. In an aqueous medium, the latter is usually ensured at pH values which do not deviate too far from 7 and at temperatures which are not excessively high. When the intimate contacting is effected in wet form, there is normally final drying to give the intimate dry mixture to be thermally treated in accordance with the invention (for example by spray-drying). In the case of dry mixing, such a dry mass is obtained automatically. It will be appreciated that the phases B and, where appropriate, C preformed in finely divided form may also be incorporated into a plastically reshapeable mixture which comprises the sources of the elemental constituents of the multimetal oxide composition A, as recommended by DE-A 10046928. The intimate contacting of the constituents of the starting compositions 1 and, where appropriate, 2 with the sources of the multielement oxide composition A (starting composition 3) may of course also be effected as described in DE-A 19815281.

The thermal treatment to obtain the active composition and the shaping may be effected as described for the multimetal oxide active compositions IV to VI.

Quite generally, multimetal oxide active composition IV to VII catalysts may advantageously be prepared in accordance with the teaching of DE-A 103 25 487 or DE-A 103 25 488.

The performance of one reaction stage (within one oxidation reactor line of the process according to the invention) from propene to acrolein can be carried out with the catalysts described as suitable for the fixed catalyst bed in question, in the simplest manner and appropriately from an application point of view, in a tube bundle reactor charged with the fixed bed catalysts, as described, for example, in EP-A 700 714 or DE-A 4 431 949 or WO 03/057653, or WO 03/055835, or WO 03/059857, or WO 03/076373.

In other words, in the simplest manner, the fixed catalyst bed is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor is generally from 250 to 450° C., frequently from 300 to 400° C. or from 300 to 380° C. The associated reaction temperatures also then move within these temperature ranges. Suitable heat exchange media are in particular fluid heating media. It is particularly appropriate to use melts of salts such as potassium nitrate, potassium nitrite, sodium nitrite and/or sodium nitrate, or of low-melting metals such as sodium, mercury and also alloys of different metals. Ionic liquids can also be used.

Appropriately, the starting reaction gas mixture is fed to the charge of fixed bed catalyst preheated to the desired reaction temperature.

Advantageously, the starting reaction gas mixture is completed in the process according to the invention beforehand, and the at least two oxidation reactor systems operated in parallel are subsequently charged simultaneously with this starting reaction gas mixture using a corresponding distributor system.

Especially in the case of desired high (e.g. $\geq$130 l (STP)/l·h, or $\geq$140 l (STP)/l·h, or $\geq$150 l (STP)/l·h, or $\geq$160 (STP)/l·h, but generally $\leq$600 l (STP)/l·h, frequently $\leq$350 l (STP)/l·h) hourly space velocities of propene on the fixed catalyst bed, a propene partial oxidation to acrolein is appropriately carried out in a two- or multizone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable. Another process description is given by EP-A 1106598.

In other words, in a simple manner, the at least one fixed catalyst bed to be used in accordance with the invention is then disposed in the uniformly charged metal tubes of a tube bundle reactor and two substantially spatially separated heating media, generally salt melts, are conducted around the metal tubes. The tube section over which the particular salt bath extends represents a reaction zone.

For example, a salt bath A preferably flows around that section of the tubes (the reaction zone A) in which the oxidative conversion of propene (in single pass) proceeds until a conversion value in the range from 40 to 80 mol % is achieved and a salt bath B preferably flows around the section of the tubes (the reaction zone B) in which the subsequent oxidative conversion of propene (in single pass) proceeds until a conversion value of generally at least 93 mol % is achieved (if required, reaction zones A, B may be followed by further reaction zones which are kept at individual temperatures).

Within the particular temperature zone, the salt bath may in principle be conducted as in the one-zone method. The inlet temperature of the salt bath B is normally from at least 5 to 10° C. above the temperature of the salt bath A. Otherwise, the inlet temperatures may be within the temperature range for the inlet temperature recommended for the one-zone method.

Otherwise, the two-zone high-load method for the propene partial oxidation to acrolein may be carried out as described, for example, in DE-A 10 30 8836, EP-A 11 06 598, or as described in WO 01/36364, or DE-A 19 92 7624, or DE-A 19 94 8523, DE-A 103 13 210, DE-A 103 13 213 or as described in DE-A 199 48 248.

Generally, the process according to the invention in a propene partial oxidation to acrolein is suitable for propene hourly space velocities on the fixed catalyst bed of $\leq$70 l (STP)/l·h, or $\geq$70 l (STP)/l·h, $\geq$90 l (STP)/l·h, $\geq$110 l (STP)/l·h, $\geq$130 l (STP)/l·h, $\geq$140 l (STP)/l·h, $\geq$160 l (STP)/l·h, $\geq$180 l (STP)/l·h, $\geq$240 l (STP)/l·h, $\geq$300 l (STP)/l·h, but normally $\leq$600 l (STP)/l·h. Here, the hourly space velocity is based on the volume of the fixed catalyst bed excluding any sections used which consist exclusively of inert material (as is generally the case in this document, unless explicitly stated otherwise).

Advantageously in accordance with the invention, the hourly space velocities on the relevant at least two oxidation reactor systems operated in parallel will be selected identically.

To prepare the fixed catalyst bed for an inventive partial oxidation of propene to acrolein, it is possible to use in the process according to the invention only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation of propene to acrolein (and consist of inert material) (shaped diluent bodies). Useful materials for such inert shaped bodies are in principle all of those which are also suitable as support materials for "propene-to-acrolein" coated catalysts. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. The inert shaped diluent bodies selected will preferably be those whose geometry corresponds to that of the first-stage shaped catalyst bodies to be diluted by them.

In general, it is favorable when the chemical composition of the active composition used for the described propene partial oxidation to acrolein does not change over the fixed catalyst bed. In other words, although the active composition used for an individual shaped catalyst body may be a mixture of different multimetal oxides comprising, for example, the elements Mo and/or W and also at least one of the elements Bi, Fe, Sb, Sn and Cu, the same mixture is then advantageously used for all shaped catalyst bodies of the fixed catalyst bed.

Advantageously in accordance with the invention, the relevant at least two oxidation reactor systems operated in parallel have oxidation reactor lines charged with catalyst in an identical manner.

In the propene partial oxidation to acrolein, the volume-specific (i.e. normalized to the unit of volume) activity preferably normally increases continuously, abruptly or in stages within the fixed catalyst bed in the flow direction of the starting reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, or catalyst activity, comprised in a certain volume of the fixed bed.

A volume-specific activity increasing at least once in the flow direction of the reaction gas mixture over the fixed catalyst bed can thus be attained in a simple manner, for example, by beginning the bed with a high fraction of inert shaped diluent bodies based on one type of shaped catalyst bodies, and then reducing this fraction of shaped diluent bodies in the flow direction either continuously or, at least once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having the higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activities may also be used for the fixed catalyst bed of an inventive propene partial oxidation to acrolein. These mixtures may in turn be diluted with inert diluent bodies.

Upstream and/or downstream of the sections, having active composition, of the fixed catalyst bed of an inventive propene partial oxidation to acrolein may be disposed beds consisting exclusively of inert material (for example only shaped diluent bodies). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4-5 mm.

In many cases, the section of the fixed catalyst bed having active composition is structured as follows for a propene partial oxidation to acrolein in the flow direction of the reaction gas mixture in the process according to the invention (according to the invention, preferably in all of the at least two oxidation reactor systems operated in parallel in accordance with the invention and in the same way).

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total lengths of the section of the fixed bed catalyst charge having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 5 to 40% by weight, preferably from 10 to 40% by weight or from 20 to 40% by weight and more preferably from 25 to 35% by weight. Downstream of this first zone is then frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies diluted only to a lesser extent (than in the first zone), or, most preferably, a sole bed of the same shaped catalyst bodies which have also been used in the first zone.

The aforementioned is especially true when the shaped catalyst bodies used in the fixed catalyst bed are unsupported catalyst rings or coated catalyst rings (especially those which are listed in this document as preferred). For the purposes of the aforementioned structuring, both the shaped catalyst bodies or their support rings and the shaped diluent bodies in the process according to the invention advantageously have substantially the ring geometry 5 mm×3 mm×2 mm (external diameter×length×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 1 or 5 to 20% generally begins the fixed catalyst bed in the flow direction of the reaction gas mixture. It is normally used as a heating zone for the reaction gas mixture.

Typically, the catalyst tubes in the tube bundle reactors for the stage of partial oxidation of propene to acrolein are manufactured from ferritic steel and typically have a wall thickness of from 1 to 3 mm. Their internal diameter is generally (uniformly) from 20 to 30 mm, frequently from 21 to 26 mm.

Appropriately from an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 are usually exceptional for this reaction stage. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

The performance of the reaction stage from acrolein to acrylic acid can be carried out with the catalysts described as suitable for the fixed catalyst bed of this reaction, likewise in the simplest manner and appropriately from an application point of view, in a tube bundle reactor charged with the fixed bed catalysts, as described, for example, in EP-A 700 893 or DE-A 4 431 949 or WO 03/057653, or WO 03/055835, or WO 03/059857, or WO 03/076373.

In other words, in the simplest manner, the fixed catalyst bed to be used is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor (in this document, this corresponds to the temperature of the fixed catalyst bed) is generally from 220 to 350° C., frequently from 245 to 285° C. or from 245 to 265° C. Suitable heat exchange media are in particular fluid heating media. It is particularly appropriate to use melts of salts such as potassium nitrate, potassium nitrite, sodium nitrite and/or sodium nitrate, or of low-melting metals such as sodium, mercury and also alloys of different metals. Ionic liquids can also be used.

Appropriately, the starting reaction gas mixture is fed to the charge of fixed bed catalyst preheated to the desired reaction temperature.

Especially in the case of desired high (e.g. $\geq$130 l (STP)/l·h, or $\geq$140 l (STP)/l·h, but generally $\leq$350 l (STP)/l·h, or $\leq$600 l (STP)/l·h) hourly space velocities of acrolein on the fixed catalyst bed, the process according to the invention for an acrolein partial oxidation to acrylic acid is appropriately carried out in a two- or multizone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable.

In other words, in a simple manner, the at least one fixed catalyst bed to be used in accordance with the invention is disposed in the uniformly charged metal tubes of a tube bundle reactor and two substantially spatially separated heating media, generally salt melts, are conducted around the metal tubes. The tube section over which the particular salt bath extends represents a temperature or reaction zone.

For example, a salt bath C preferably flows around that section of the tubes (the reaction zone C) in which the oxidative conversion of acrolein (in single pass) proceeds until a conversion value in the range from 55 to 85 mol % is achieved and a salt bath D preferably flows around the section of the tubes (the reaction zone D) in which the subsequent oxidative conversion of acrolein (in single pass) proceeds until a conversion value of generally at least 90 mol % is achieved (if required, reaction zones C, D may be followed by further reaction zones which are kept at individual temperatures).

Within the particular temperature zone, the salt bath may in principle be conducted as in the one-zone method. The inlet temperature of the salt bath D is normally from at least 5 to 10° C. above the temperature of the salt bath C. Otherwise, the inlet temperatures may be within the temperature range for the inlet temperature recommended for the one-zone method.

Otherwise, the two-zone high-load method for the acrolein partial oxidation to acrylic acid may be carried out as described, for example, in DE-A 19 94 8523, EP-A 11 06 598 or as described in DE-A 19 94 8248.

Accordingly, the process according to the invention is suitable for acrolein hourly space velocities on the fixed catalyst bed of $\leq$70 l (STP)/l·h, or $\geq$70 l (STP)/l·h, $\geq$90 l (STP)/l·h, $\geq$110 l (STP)/l·h, $\geq$130 l (STP)/l·h, $\geq$180 l (STP)/l·h, $\geq$240 l (STP)/l·h, $\geq$300 l (STP)/l·h, but normally $\leq$600 l (STP)/l·h. Here, the hourly space velocity is based on the volume of the fixed catalyst bed excluding any sections used which consist exclusively of inert material.

To prepare the at least one fixed catalyst bed, it is possible to use, for an inventive partial oxidation of acrolein to acrylic acid, only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation (and consist of inert material) (shaped diluent bodies). Useful materials for such inert shaped bodies are in principle all of those which are also suitable as support materials for "acrolein-to-acrylic acid coated catalysts" which are suitable in accordance with the invention. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. According to the invention, the inert shaped diluent bodies selected will preferably be those whose geometry corresponds to that of the shaped catalyst bodies to be diluted by them.

In general, it is favorable in the context of an inventive partial oxidation of acrolein to acrylic acid when the chemical composition of the active composition used does not change over the fixed catalyst bed. In other words, although the active composition used for an individual shaped catalyst body may be a mixture of different multimetal oxides comprising the elements Mo and V, the same mixture then advantageously has to be used for all shaped catalyst bodies of the fixed catalyst bed.

For an inventive partial oxidation of acrolein to acrylic acid, the volume-specific (i.e. normalized to the unit of volume) activity preferably normally increases continuously, abruptly or in stages within the fixed catalyst bed in the flow direction of the reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, or catalyst activity, in a certain volume of the fixed bed.

A volume-specific activity increasing at least once in the flow direction of the reaction gas mixture over the fixed catalyst bed can thus be attained in a simple manner for a process for acrolein partial oxidation to acrylic acid according to the invention, for example, by beginning the bed with a high fraction of inert shaped diluent bodies based on one type of shaped catalyst bodies, and then reducing this fraction of shaped diluent bodies in the flow direction either continuously or, at least once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having the higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activities may also be used for the fixed catalyst bed of an inventive acrolein partial oxidation to acrylic acid. These mixtures may in turn be diluted with inert diluent bodies.

Upstream and/or downstream of the sections, having active composition, of the fixed catalyst bed may be disposed beds consisting exclusively of inert material (for example only shaped diluent bodies). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4-5 mm.

In many cases, in an inventive process for acrolein partial oxidation to acrylic acid, the section of the fixed catalyst bed having active composition is structured as follows in the flow direction of the reaction gas mixture (according to the invention, preferably in all of the at least two oxidation reactor systems operated in parallel in accordance with the invention and in the same way).

First, to a length of from 10 to 60%, preferably from 10 to 50%, more preferably from 20 to 40% and most preferably from 25 to 35% (i.e., for example, to a length of from 0.70 to 1.50 m, preferably from 0.90 to 1.20 m), each of the total length of the section of the fixed bed catalyst charge having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone is then frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies diluted only to a lesser extent (than in the first zone or in the first two zones), or, most preferably, a sole bed of the same shaped catalyst bodies which have also been used in the first zone (or in the first two zones).

The aforementioned is especially true when the shaped catalyst bodies used in the fixed catalyst bed are coated catalyst rings or coated catalyst spheres (especially those which are listed in this document as preferred for an acrolein partial oxidation to acrylic acid). For the purposes of the aforementioned structuring, both the shaped catalyst bodies or their support rings and the shaped diluent bodies in a process for acrolein partial oxidation to acrylic acid according to the invention advantageously have substantially the ring geometry 7 mm×3 mm×4 mm (external diameter×length×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 5 to 20% generally begins the fixed catalyst bed for acrolein partial oxidation in the flow direction of the reaction gas mixture. It is normally used as a heating zone for the reaction gas mixture.

Typically, the catalyst tubes in the tube bundle reactors for the inventive acrolein partial oxidation are manufactured from ferritic steel and typically have a wall thickness of from 1 to 3 mm. Their internal diameter is generally (uniformly) from 20 to 30 mm, frequently from 21 to 26 mm. Appropriately from an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 are usually exceptional for the acrolein partial oxidation. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

As already described, both the propene and the acrolein partial oxidation in the process according to the invention may be carried out in one-zone or in two-zone tube bundle reactors. When the two reaction stages are connected in series, it is also possible for only the first reaction stage to be carried out in a one-zone tube bundle reactor and the second reaction stage in a two-zone tube bundle reactor (or vice versa). In this case, the product gas mixture of the first reaction stage (preferably after mixing over all oxidation reactor systems operated in parallel) is, if appropriate after supplementation with inert gas or with molecular oxygen or with inert gas and molecular oxygen, and also if appropriate on completion of direct and/or indirect intermediate cooling, fed directly to the second reaction stage.

Between the tube bundle reactors of the first and the second reaction stage may be disposed an intermediate cooler which may optionally comprise inert beds.

It will be appreciated that the fixed catalyst bed of the propene partial oxidation and the fixed catalyst bed of the acrolein partial oxidation for the inventive process of a two-stage partial oxidation of propene to acrylic acid may also be accommodated spatially successively in a single multiple-catalyst-tube tube bundle reactor likewise having, for example, two temperature zones or more, as described, for example, by WO 03/059857, EP-A 911313 and EP-A 990636. This case is referred to as a singlereactor two-stage process. In this case, one or two temperature zones generally extend over one fixed catalyst bed. Between the two fixed catalyst beds may additionally be disposed an inert bed which is, if appropriate, disposed in a third temperature zone and is heated separately. The catalyst tubes may be continuous or interrupted by the inert bed.

The inert gas to be used for the charge gas mixture of the "propene-to-acrolein reaction stage" (the starting reaction gas mixture 1) may, irrespective of the propene hourly space velocity selected for the fixed catalyst bed (and irrespective of whether there is a downstream "acrolein-to-acrylic acid reaction stage"), consist, for example, of $\geq$20% by volume, or $\geq$30% by volume, or $\geq$40% by volume, or $\geq$50% by volume, or $\geq$60% by volume, or $\geq$70% by volume, or $\geq$80% by volume, or $\geq$90% by volume, or $\geq$95% by volume, of molecular nitrogen.

However, the inert diluent gas may also consist, for example, of from 2 to 35 or 20% by weight of $H_2O$ and from 65 to 98% by volume of $N_2$.

However, at propene hourly space velocities on the fixed catalyst bed of the "propene-to-acrolein reaction stage" of above 250 l (STP)/l·h, the use of inert diluent gases such as propane, ethane, methane, butane, pentane, $CO_2$, CO, steam and/or noble gases is recommended for the process according to the invention. However, it will be appreciated that these gases may also be used even at lower propene hourly space velocities to attenuate hotspot formation.

The working pressure in the inventive gas phase partial oxidation of propene to acrolein (especially at start of the operating time of a fixed catalyst bed) may be either below atmospheric pressure (for example up to 0.5 bar) or above atmospheric pressure. Typically, the working pressure in the gas phase partial oxidation of propene will be at values of from 1 to 5 bar, frequently from 1 to 3 bar.

Normally, the reaction pressure in the inventive propene partial oxidation to acrolein will not exceed 100 bar. It will be appreciated that the inventive procedure may also be employed quite generally in combination with the procedures for prolonging the lifetime of a catalyst bed recommended in the documents EP-A 990 636, EP-A 11 06 598, EP-A 614 872, DE-A 10 35 822, DE-A 10 23 2748, DE-A 10351269 and in the German application DE-A 10 2004 025 445. It is thus possible to achieve catalyst bed lifetimes of several years.

The molar $O_2$:propene ratio in the starting reaction gas mixture 1 for the propene partial oxidation to acrolein which is conducted through the appropriate fixed catalyst bed in the process according to the invention will normally be $\geq$1 (substantially irrespective of whether there is a downstream acrolein partial oxidation stage to acrylic acid). Typically, this ratio will be at values of $\leq$3. Frequently, the molar $O_2$:propene ratio in the aforementioned charge gas mixture will advantageously be from 1:2 to 1.4:2. In many cases, the process for the propene partial oxidation to acrolein will be performed at a propene:oxygen:inert gas (including steam) volume ratio (l (STP) of 1:(1 to 3):(3 to 30), preferably of 1:(1.5 to 2.3):(10 to 15), in the starting reaction gas mixture 1.

The propene fraction in the starting reaction gas mixture 1 may lie, for example, at values of from 4 to 20% by volume, frequently from 5 or 7 to 15% by volume or from 6 or 8 to 12% by volume or from 5 to 8% by volume (based in each case on the total volume).

A typical composition of the starting reaction gas mixture 1 (irrespective of the hourly space velocity selected and irrespective of whether an acrolein partial oxidation stage to acrylic acid follows) may comprise the following components:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.01 to 0.04% by volume of acrolein,
from 10.4 to 10.7% by volume of $O_2$ and,
as the remainder ad 100%, molecular nitrogen, or:

5.4% by volume of propene,
10.5% by volume of oxygen,
1.2% by volume of $CO_x$,
80.5% by volume of $N_2$ and
2.4% by volume of $H_2O$.

However, the starting reaction gas mixture 1 for the propene partial oxidation to acrolein may, in accordance with the invention, also have the following composition:

from 6 to 15% by volume of propene,
from 4 to 30% by volume (frequently from 6 to 15% by volume) of water,
from $\geq$0 to 10% by volume (preferably from $\geq$0 to 5% by volume) of constituents other than propene, water, oxygen and nitrogen, sufficient molecular oxygen that the molar ratio of molecular oxygen present to molecular propene present is from 1.5 to 2.5, and, as the remainder up to 100% by volume of the total amount, molecular nitrogen.

Another possible starting reaction gas mixture 1 composition for the propene partial oxidation to acrolein may, in accordance with the invention, comprise:

6.0% by volume of propene,
60% by volume of air and
34% by volume of $H_2O$.

Alternatively, starting reaction gas mixtures 1 of the composition according to Example 1 of EP-A 990 636, or according to Example 2 of EP-A 990 636, or according to Example 3 of EP-A 1 106 598, or according to Example 26 of EP-A 1 106 598, or according to Example 53 of EP-A 1 106 598, may also be used for the "propene-to-acrolein reaction stage".

Further starting reaction gas mixtures 1 for the "propene-to-acrolein reaction stage" which are suitable in accordance with the invention may lie within the following composition framework:

from 7 to 11% by volume of propene,
from 6 to 12% by volume of water,
from $\geq 0$ to 5% by volume of constituents other than propene, water, oxygen and nitrogen,
sufficient molecular oxygen that the molar ratio of oxygen present to molecular propene present is from 1.4 to 2.2, and,
as the remainder up to 100% by volume of the total amount, molecular nitrogen.

The propene to be used in the starting reaction gas mixture 1 is in particular polymergrade propene and chemical-grade propene, as described, for example, by DE-A 10232748. In a manner advantageous in accordance with the invention, a heterogeneously catalyzed dehydrogenation and/or oxydehydrogenation of propane to propene, as described, for example, by the documents DE-A 102 45 585, WO 03/076370, DE-A 103 16 039, DE-A 33 13 573, U.S. Pat. No. 3,161,670, WO 01/96270, WO 01/96271 and WO 03/011804, can serve as the propene source for an inventive heterogeneously catalyzed propene gas phase partial oxidation with molecular oxygen to acrolein and/or acrylic acid (or ammoxidation to acrylonitrile) in at least two oxidation reactor systems operated in parallel. Advantageously, the propene to be oxidized partially is accompanied by propane.

In this case, one dehydrogenation reactor preferably serves at least two oxidation reactor systems operated in parallel in accordance with the invention with propene.

Starting reaction gas mixture 1 then preferably lies within the following composition framework:

from 7 to 15% by volume of $O_2$,
from 5 to 10% by volume of propylene,
from 10 or 15 to 40% by volume of propane,
from 25 to 60% by volume of nitrogen,
from 1 to 5% by volume of sum of CO, $CO_2$ and $H_2O$ and
from 0 to 5% by volume of other constituents,
without taking into account any ammonia comprised.

It should also be mentioned at this point that, irrespective of whether an "acrolein-to-acrylic acid reaction stage" follows, a portion of the charge gas mixture of the "propene-to-acrolein reaction stage" may be what is known as cycle gas. As already described, this is gas which remains after the target product removal from the product gas in the removal system (for acrolein and/or acrylic acid) which follows the oxidation reactor system in accordance with the invention, and is generally recycled partly as a substantially inert diluent gas to charge the propene reaction stage and/or any subsequent acrolein reaction stage.

The oxygen source used is normally air.

The hourly space velocity on the fixed catalyst bed (excluding pure inert sections) of starting reaction gas mixture 1, in particular in a process according to the invention for preparing acrolein and/or acrylic acid from propere, will typically be from 1000 to 10 000 l (STP)/l·h, usually from 1000 to 5000 l (STP)/l·h, frequently from 1500 to 4000 l (STP)/l·h.

When the propene partial oxidation to acrolein is followed by an acrolein partial oxidation, the product gas mixture of the propene reaction stage is, if appropriate after intermediate cooling, fed to the acrolein reaction stage. Advantageously in accordance with the invention, the product gas streams of the at least two propene partial oxidations to acrolein are mixed with one another beforehand. The oxygen required in the acrolein reaction stage may already have been added to the starting reaction gas mixture 1 for the propene reaction stage as an excess and thus be a constituent of the product gas mixture of the propene reaction stage. In this case, the product gas mixture of the propene reaction stage, intermediately cooled if appropriate, may directly be the charge gas mixture of the acrolein reaction stage. However, some or all of the oxygen required for the second oxidation step from acrolein to acrylic acid may also not be added to the product gas mixture of the propene reaction stage until it enters the acrolein reaction stage, for example in the form of air. This addition may be associated with direct cooling of the product gas mixture of the acrolein reaction stage.

Resulting from the aforementioned connection, the inert gas present in the charge gas mixture for an acrolein reaction stage (the starting reaction gas mixture 2) (irrespective of whether there is a preceding propene reaction stage) may consist of, for example, $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

However, the inert diluent gas in the charge gas for the acrolein reaction stage will frequently consist of from 5 to 25 or 20% by weight of $H_2O$ (may be formed, for example, in a preceding propene reaction stage and/or added if appropriate) and of from 70 to 90% by volume of $N_2$.

However, at acrolein hourly space velocities on the fixed catalyst bed for the partial oxidation of acrolein to acrylic acid of above 250 l (STP)/l·h, the use of inert diluent gases such as propane, ethane, methane, butane, pentane, $CO_2$, steam and/or noble gases is recommended for the process according to the invention. However, it will be appreciated that these gases may also be used even at lower acrolein hourly space velocities.

The working pressure in the inventive gas phase partial oxidation of acrolein to acrylic acid (especially at the start of the operating time of a fixed catalyst bed) may be either below atmospheric pressure (for example up to 0.5 bar) or above atmospheric pressure. Typically, the working pressure in the gas phase partial oxidation of acrolein will be at values of from 1 to 5 bar, frequently from 1 to 3 bar.

Normally, the reaction pressure in the inventive acrolein partial oxidation will not exceed 100 bar. It will be appreciated that the inventive procedure may also be employed quite generally in combination with the procedures for prolonging the lifetime of a catalyst bed recommended in the documents EP-A 990 636, EP-A 11 06 598, EP-A 614 872, DE-A 10 35 0822, DE-A 10 23 2748, DE-A 10351269 and in the German application DE-A 10 2004 025 445. It is thus possible to achieve catalyst bed lifetimes of several years.

The molar $O_2$:acrolein ratio in the charge gas mixture for an acrolein reaction stage which is conducted through the appropriate fixed catalyst bed in the process according to the invention (irrespective of whether there is a preceding propene reaction stage or not) will normally be $\geq 1$. Typically, this ratio will be at values of $\leq 3$. According to the invention, the molar $O_2$:acrolein ratio in the aforementioned charge gas mixture will frequently be from 1 to 2 or from 1 to 1.5. In many cases, the process according to the invention will be performed at an acrolein:oxygen:steam:inert gas volume ratio (l (STP)) of 1:(1 to 3):(0 to 20):(3 to 30), preferably of 1:(1 to 3):(0.5 to 10):(7 to 20), in the starting reaction gas mixture 2 (charge gas mixture for the acrolein reaction stage).

The acrolein fraction in the charge gas mixture for the acrolein reaction stage may lie, for example, (irrespective of whether there is a preceding propene reaction stage or not) at values of from 3 or 6 to 15% by volume, frequently from 4 or 6 to 10% by volume, or from 5 to 8% by volume (based in each case on the total volume). The hourly space velocity on the fixed catalyst bed (here excluding pure inert sections) of charge gas mixture (starting reaction gas mixture 2) in an inventive "acrolein-to-acrylic acid process" will typically be, as for the "propene-to-acrolein reaction stage", from 1000 to 10 000 l (STP)/l·h, usually from 1000 to 5000 l (STP)/l·h, frequently from 1500 to 4000 l (STP)/l·h.

When the process according to the invention is practiced, fresh fixed catalyst beds for the partial oxidation of propene to acrolein will normally be operated in such a way that, after determining the composition of starting reaction gas mixture 1 and determining the hourly space velocity on the fixed catalyst beds for the propene partial oxidation of starting reaction gas mixture 1, the temperature of the fixed catalyst beds (or the inlet temperature of the heating medium into the heating zone of the tube bundle reactor) is adjusted in such a way that the conversion $C^{pro}$ of propene on single pass of reaction gas mixture 1 through the fixed catalyst beds is at least 93 mol %. When favorable catalysts are used, values for $C^{pro}$ of $\geq$94 mol %, or $\geq$95 mol %, or $\geq$96 mol %, or $\geq$97 mol % and frequently even more are also possible.

When the heterogeneously catalyzed partial oxidation of propene to acrolein is practiced continuously, the composition of starting reaction gas mixture 1 and the hourly space velocity on the corresponding fixed catalyst beds of starting reaction gas mixture 1 will be kept substantially constant (if appropriate, the hourly space velocity is adjusted to the fluctuating market demand). A fall in the activity of the fixed catalyst beds over time will normally be initially counteracted under these production conditions by increasing the temperature of the fixed catalyst beds (the inlet temperature of the heating medium into the temperature zone of the tube bundle reactors) from time to time (the flow rate of the heating medium is likewise normally substantially retained), in order to keep the propene conversion in single pass of the reaction gas mixture within the desired target corridor (i.e. at $C^{pro}$ of $\geq$93 mol %, or $\geq$94 mol %, or $\geq$95 mol %, or $\geq$96 mol %, or $\geq$97 mol %).

The further procedure will therefore advantageously be to interrupt the gas phase partial oxidation from time to time in accordance with the invention, in order to conduct a gas mixture G consisting of molecular oxygen, inert gas and, if appropriate, steam through the fixed catalyst bed at a temperature of the fixed catalyst bed of from 250 to 550° C. as described in DE-A 10351269. Subsequently, the partial oxidation of propene is continued while substantially retaining the process conditions (the propene hourly space velocity on the fixed catalyst beds is preferably restored slowly) and the temperature of the fixed catalyst beds is adjusted in such a way that the propene conversion attains the desired target value. In general, this temperature value, for the same conversion, will be at a somewhat lower value than the temperature that the fixed catalyst bed had before the interruption of the partial oxidation and the treatment with the gas mixture G. Starting from this temperature value of the fixed catalyst beds, the partial oxidation is continued while substantially retaining the remaining conditions, and the fall in the activity of the fixed catalyst beds over time is appropriately in turn counteracted by increasing the temperature of the fixed catalyst beds from time to time. Within, for example, one successive calendar year, the partial oxidation, appropriately in accordance with the invention, is in turn interrupted at least once, in order to conduct the gas mixture G through the fixed catalyst beds. Afterward, the partial oxidation is started up again as described, etc. When the target product selectivity achieved is no longer satisfactory, a partial or full catalyst change will be carried out as described, for example, in one of the at least two relevant oxidation reactor lines and the further procedure will subsequently be in accordance with the invention.

In a corresponding manner, when practicing the process according to the invention, fresh fixed catalyst beds for the partial oxidation of acrolein to acrylic acid will normally be operated in such a way that, after determining the operation of this reaction stage and the composition of starting reaction gas mixture 2 and determining the hourly space velocity on the appropriate fixed catalyst beds of starting reaction gas mixture 2, the temperature of the fixed catalyst beds (or the inlet temperature of the heating medium into the heating zone of the tube bundle reactors) is adjusted in such a way that the conversion $C^{acr}$ of acrolein in single pass of starting reaction gas mixture 2 through the fixed catalyst beds is at least 90 mol %. When favorable catalysts are used, values for $C^{acr}$ of $\geq$92 mol %, or $\geq$94 mol %, or $\geq$96 mol %, or $\geq$98 mol %, and frequently even $\geq$99 mol % and more are also possible.

When the heterogeneously catalyzed partial oxidation of acrolein to acrylic acid is practiced continuously, the composition of starting reaction gas mixture 2 and the hourly space velocity on the corresponding fixed catalyst beds of starting reaction gas mixture 2 will be kept substantially constant (if appropriate, the hourly space velocity is adjusted to the fluctuating market demand). A fall in the activity of the fixed catalyst beds over time will normally be counteracted under these production conditions by increasing the temperature of the fixed catalyst beds (the inlet temperature of the heating medium into the temperature zone of the tube bundle reactor) from time to time (the flow rate of the heating medium is likewise normally substantially retained), in order to keep the acrolein conversion in single pass of the charge gas mixture within the desired target corridor (i.e. at values of $\geq$90 mol %, or $\geq$92 mol %, or $\geq$94 mol %, or $\geq$96 mol %, or $\geq$98 mol %, or $\geq$99 mol %).

The further procedure will therefore advantageously be to interrupt the gas phase partial oxidation at least once, for example before the undertaken temperature increase of the fixed catalyst beds is permanently $\geq$10° C. or $\geq$8° C. (based on the temperature of the same fixed catalyst bed set beforehand), in order to conduct the gas mixture G through the fixed catalyst bed of the partial oxidation of acrolein to acrylic acid (in a two-stage partial oxidation of propene to acrylic acid, conducting it via the fixed catalyst beds of the propene oxidation of acrolein) at a temperature of the fixed catalyst beds of from 200 to 450° C. Subsequently, the partial oxidation is continued while substantially retaining the process conditions (the acrolein hourly space velocity on the appropriate fixed catalyst bed is preferably restored slowly, as described, for example, in DE-A 10337788) and the temperature of the fixed catalyst beds is adjusted in such a way that the acrolein conversion attains the desired target value. In general, this temperature value, for the same conversion, will be at a somewhat lower value than the temperature that the fixed catalyst bed had before the interruption of the partial oxidation and the treatment with the gas mixture G. Starting from this temperature value of the fixed catalyst bed, the partial oxidation of acrolein is continued while substantially retaining the remaining conditions, and the fall in the activity of the fixed catalyst beds over time is appropriately in turn counteracted by increasing the temperature of the fixed catalyst beds from time to time. For example, before the temperature increase of the fixed catalyst beds which has been carried out is permanently $\geq$10° C. or $\geq$8° C., the partial oxidation is in turn interrupted, in order to conduct the gas mixture G through the fixed catalyst bed of the acrolein partial oxidation of acrolein to acrylic acid (if appropriate conducting it via the fixed catalyst bed of a propene reaction stage). Afterward, the partial oxidation is started up again as described, etc. When the target product selectivity achieved is no longer satisfactory, a partial or full catalyst change will be carried out as described, for example, in one of the at least two relevant oxidation lines and the further procedure will subsequently be in accordance with the invention.

Generally, an acrolein-to-acrylic acid heterogeneously catalyzed partial oxidation should be operated in such a way that the oxygen content in the resultant product gas stream is still from 1.5 to 3.5% by volume.

Preferably in accordance with the invention, the removal of acrylic acid will be undertaken from the mixture of the product gas streams. This acrylic acid removal and the generally accompanying cycle gas formation can be undertaken in a target product removal line, as described, for example, in the documents WO 97/48669, US-A 2004/0242826, WO 01/96271 and U.S. Pat. No. 6,410,785.

Since the separating action of separating columns normally grows with increasing number of theoretical plates, it is possible in accordance with the invention, for example, to achieve the desired purity of the crude target product over longer operating times with smaller (i.e. having a smaller number of theoretical plates) and thus less expensive separating columns.

When ($\geq 2$) oxidation reactor systems are operated in the inventive manner in such a way that the mixture stream comprises target compounds from all n oxidation reactor systems, it is favorable in accordance with the invention when the operating age of the n catalyst charges of the n oxidation reactor systems are offset in time on the time axis in such a way that the operating age difference between successive points on the time axis is substantially equally large and no two points coincide.

Expressed in another way, the present invention comprises a process for preparing at least one organic target compound, which comprises:
a) the heterogeneously catalyzed gas phase partial oxidation of at least one organic precursor compound with molecular oxygen in two oxidation reactor systems which comprise catalyst charges and are operated in parallel to obtain two product gas streams each comprising the target compound, of which one stems from one of the two oxidation reactor systems and
b) subsequent removal of the at least one target compound from the two product gas streams to obtain a crude target product stream, in which,
c) before the removal, missing together the two product gas streams, or, in the course of the removal, missing together two of any target product-comprising subsequent streams obtained on the route from the two product gas streams to the one crude target product stream, and/or, after the removal from the two product gas streams, missing together crude target product streams obtained in the course of the removal, to give a mixture stream,
wherein
one of the two catalyst charges of the two oxidation reactor systems operated in parallel comprises at least one portion of catalyst over which the heterogeneously catalyzed gas phase partial oxidation has already been carried out for longer than over all portions of catalyst of the other catalyst charge.

Of course, more than one organic target compound may be obtained simultaneously in the process according to the invention. An example thereof is the propane partial oxidation, in which acrolein and acrylic acid are generally formed simultaneously. In a similar manner, acrylic acid and acrylonitrile can be formed simultaneously in a partial ammoxidation of propene and/or propane when the ammonia content of the reaction gas mixture is appropriately selected substoichiometrically. Alternatively, the starting material can also be a reaction gas mixture which comprises more than one precursor compound. Finally, it should be emphasized that the principle of the inventive procedure can also be applied analogously to catalyzed esterifications or to other catalyzed reactions. It is also essential to the invention that a secondary component outlet always forms the on-spec target compound.

The present invention also comprises processes as described above, and also wherein the at least one organic target compound has at least one ethylenically unsaturated carbon-carbon double bond and which is followed by a process for preparing polymers, into which of the at least one organic target compound is polymerized; or wherein the at least one organic target compound has at least one carboxyl group and which is followed by a process for preparing esters of the organic target compound by reacting them with an alcohol; or wherein the at least one organic target compound additionally has at least one ethylenically unsaturated carbon-carbon double bond and which is followed by a process for preparing polymers, into which at least one ester is polymerized. The organic target compound may in particular be acrylic acid and/or methacrylic acid. Useful alcohols (for example mono- or polyhydric) are especially alkanols, in particular $C_1$- to $C_8$-alkanols (in particular monohydric), i.e., for example, methanol, ethanol, 2-ethylhexanol, n-butanol and/or tert-butanol.

An apparatus according to the present invention is exemplified in the Figure, wherein the numbers therein have the following meaning:
6=two oxidation reactor systems, each system charged with catalyst, with the catalyst in one reactor system having generated more target product than generated by the catalyst charged in the other reactor system at any particular time;
1=line for the reaction starting gas mixture feed comprising the relevant organic starting material;
5(1) and 5(2)=lines for the target product comprising product gas of the respective reactor system;
5=line for the combination of the two product gases;
7=absorption column for the partial condensation of the product gas;
3=outlet for the target product absorbed in the absorbent;
4=outlet for nonabsorbables; and
2=inlet for the absorbent.

EXAMPLES AND COMPARATIVE EXAMPLES

Two-Stage Heterogeneously Catalyzed Gas Phase Partial Oxidation of Propene to Acrylic Acid A) General Experimental Construction
I. Reactors for the First Reaction Stage from Propene to Acrolein A reactor consisted of a jacketed cylinder made of stainless steel (cylindrical guide tube, surrounded by a cylindrical outer vessel). The wall thicknesses were universally from 2 to 5 mm.

The internal diameter of the outer cylinder was 91 mm. The internal diameter of the guide tube was approx. 60 mm.

At the top and bottom, the jacketed cylinder was concluded by a lid and bottom respectively.

The catalyst tube (total length 400 cm, internal diameter 26 mm, external diameter 30 mm, wall thickness 2 mm, stainless steel) was conducted through the cylindrical guide tube and accommodated in the cylindrical vessel in such a way that it in each case just projected through the lid and bottom at the upper and lower end thereof (with sealing). The heat exchange medium (salt melt consisting of 53% by weight of potassium nitrate, 40% by weight of sodium nitrite and 7% by weight of sodium nitrate) was disposed in the cylindrical vessel with connection into the guide tube. In order to ensure very uniform thermal boundary conditions at the outer wall of the catalyst tube over the entire catalyst tube length (400 cm), the heat exchange medium was pumped by means of a propeller pump first through the cylindrical vessel for the purpose of heating it and then through the intermediate space between guide tube and catalyst tube for the purpose of heating the catalyst tube. Subsequently, it was recycled into the cylindrical vessel.

An electrical heater mounted on the outer jacket of the cylindrical vessel controlled the temperature of the heat exchange medium to the desired level. Otherwise, there was air cooling.

Reactor charge: Viewed over the first-stage reactor, salt melt and starting reaction gas mixture 1 were conducted in cocurrent. Starting reaction gas mixture 1 entered the catalyst tube at the bottom. It was conducted into the catalyst tube in each case at a temperature of 165° C.

The salt melt likewise entered the cylindrical guide tube at the bottom at a temperature $T^{in}$ and exited from the cylindrical guide tube at the top at a temperature $T^{out}$ which was up to 2° C. above $T^{in}$. The inlet temperature $T^{in}$ was always such (approx. 320° C.) that a propene conversion of 97.5±0.1 mol % in single pass of the reaction gas mixture through the catalyst tube resulted in all cases.

Catalyst tube charge:
(from bottom to top) Section A: length 90 cm
  Preliminary bed of steatite spheres of diameter 4-5 mm.
Section B: length 100 cm
  Catalyst charge with a homogeneous mixture of 30% by weight of steatite rings of geometry 5 mm×3 mm×2 mm (external diameter×length×internal diameter) and 70% by weight of unsupported catalyst from Section C.
Section C: length 200 cm
  Catalyst charge of annular (5 mm×3 mm×2 mm=external diameter×length×internal diameter) unsupported catalyst according to Example 1 of DE-A 10046957 (stoichiometry: $[Bi_2W_2O_9.2WO_3]_{0.5}$ $[Mo_{12}Co_{5.5}Fe_{2.94}Si_{1.59}K_{0.08}O_x]_1$).
Section D: length 10 cm
  Downstream bed of steatite rings of geometry 7 mm×3 mm×4 mm (external diameter×length×internal diameter).

Two reactors as described above were operated in parallel.

II. Intermediate Cooling and Possible Intermediate Oxygen Feeding (Air as Secondary Gas)

The product gas streams leaving the two first-stage reactors were conducted for the purpose of intermediate cooling (indirectly by means of air) together through a connecting tube (length 40 cm, internal diameter 26 mm, external diameter 30 mm, wall thickness 2 mm, stainless steel, wound around by 1 cm of insulation material) which, mounted centrally for a length of 20 cm, was charged with an inert bed of steatite rings of geometry 7 mm×3 mm×4 mm (external diameter×length×internal diameter) and flanged directly in a Y-shape onto the first-stage catalyst tubes.

In all cases, the mixture of the product gas streams entered the connecting tube at a temperature of more than 320° C. and exited from it at a temperature above 200° C. and below 270° C.

At the end of the connecting tube, it was possible to meter air compressed to the pressure of the mixture stream as required to the cooled mixture of the product gas streams. The resulting reaction gas mixture 2 was conducted in equal parts directly into the two second-stage catalyst tubes arranged in parallel, to which the above-mentioned connecting tube was likewise flanged in a Y-shape by its other end.

III. Reactors for the Second Reaction Stage of Acrolein to Acrylic Acid

Catalyst tube fixed bed reactors were used which were of identical design to those for the first reaction stage. Salt melt and reaction gas mixture were likewise conducted in cocurrent viewed over the individual reactor. The salt melt entered the guide tube at the bottom, starting reaction gas mixture 2 likewise. The inlet temperature $T^{in}$ of the salt melt was always adjusted in such a way (approx. 26.3° C.) that an acrolein conversion of 99.3±0.1 mol % in single pass of the reaction gas mixture resulted in all cases. $T^{out}$ of the salt melt was up to 2° C. above $T^{in}$.

The catalyst tube charge (from bottom to top) was:
Section A: length 70 cm
  Preliminary bed of steatite rings of geometry 7 mm×3 mm×4 mm (external diameter×length×internal diameter).
Section B: Length 100 cm
  Catalyst charge with a homogeneous mixture of 30% by weight of steatite rings of geometry 7 mm×3 mm×4 mm (external diameter×length×internal diameter) and 70% by weight of coated catalyst from Section C.
Section C: Length 200 cm
  Catalyst charge with annular (7 mm×3 mm×4 mm=external diameter×length×internal diameter) coated catalyst according to Preparation Example 5 of DE-A 100 46 928 (stoichiometry: $Mo_{12}V_3W_{1.2}Cu_{2.4}O_x$).
Section D: Length 30 cm
  Downstream bed of steatite spheres of diameter 4-5 mm.

IV. Removal of Acrylic Acid from the Mixture of the Product Gas Streams of the Second Reaction Stage The two product gas streams coming from the second reaction stages were combined and the resulting product gas stream was subjected to a direct cooling by means of water which comprised 350 ppm by weight of hydroquinone (HQ) as a polymerization inhibitor (temperature=4° C.) in a Venturi separator (equate to the design of Venturi tubes and accelerate the gas mixture at the narrowest point of the Venturi tube, simultaneously inject the cooling water and mix intensively in the turbulent flow field giving high pressure drops; downstream separators separate the liquid phase), and the resulting mixture is fed to a liquid phase separator. A heat exchanger was used to recycle the separated aqueous phase into the Venturi separator (360 l/h). Excess aqueous phase was removed continuously.

The mixture gas stream cooled to a temperature of 30° C. was conducted from the bottom into an absorption column which comprised 11 bubble-cap trays in equidistant arrangement (tray separation: 54 mm; tray diameter: 12 mm) and exposed to the countercurrent of 1.10 kg/h of HQ-stabilized water as an absorbent (introduced at the top of the column with a temperature of 2° C.). 1.7 kg per hour of approx. 40% by weight aqueous acrylic acid were withdrawn from the bottom of the column. The residual gas leaving the absorption column at the top was, as required, sent to incineration and/or used as cycle gas for the formation of starting reaction gas mixture 1 (recycled via a compressor to the first-stage reactors).

B) Results Achieved as a Function of the Catalyst Charges and of the Composition of the Starting Reaction Gas Mixtures Comparative Example 1

Both first-stage reactors and both second-stage reactors were charged with fresh catalysts.

The composition of the starting reaction gas mixture fed to the two first-stage reactors was:
- 5.3% by volume of propene,
- 2.4% by volume of water,
- 0.7% by volume of constituents other than propene, water, oxygen and nitrogen,
- molecular oxygen in an amount such that the molar ratio of molecular oxygen comprised to propene comprised was 1.52, and
- as the remainder up to 100% by volume, molecular nitrogen.

The propene hourly space velocity on the two first-stage catalyst tube charges was 110 l (STP)/l·h. The fresh oxygen source was air. The starting reaction gas mixture comprised 8% by volume of cycle gas per % by volume of fresh propene. Secondary air was metered to the mixture of the product gas streams of the first reaction stages. Their amount was such that the ratio of secondary air/fresh propene (each in l (STP)) was 1.45. This gave rise to a residual oxygen content of 3.0% by volume in the product gas of the second reaction stage. The experimental plant was thus operated continuously over 28 weeks. The selectivity of target product formation (acrylic acid) $S^{AA}$ achieved as a function of the operating time (in weeks), and also the by-product selectivities for acetic acid ($S^{HAc}$) and formaldehyde ($S^F$) achieved as a function of the operating time, each in mol % based on propene converted, are shown by Table 1 which follows (always based on the output of the second reaction stage). Table 1 likewise shows the molar ratio V of acrylic acid to acetic acid in the aqueous absorbate.

TABLE 1

| Operating time | $S^{AA}$ | $S^{HAc}$ | $S^F$ | V |
|---|---|---|---|---|
| Startup | 86.8 | 2 | 1.2 | 43.4 |
| 4 | 88 | 1.9 | 1.1 | 46.3 |
| 8 | 88.7 | 1.8 | 1.05 | 49.3 |
| 12 | 89.4 | 1.75 | 0.95 | 51.4 |
| 16 | 89.9 | 1.7 | 0.9 | 52.4 |
| 20 | 90.3 | 1.65 | 0.85 | 54.7 |
| 24 | 90.8 | 1.62 | 0.82 | 56.0 |
| 28 | 91.2 | 1.6 | 0.8 | 57 |

The further separation of the aqueous, target product-comprising absorbate has to be designed for a ratio of V=43.4.

Example 1

First, Comparative Example 1 was repeated. After the repetition of Comparative Example 1 had produced 2200 kg of acrylic acid without interruption, operation was interrupted and only the catalyst charge of one of the two oxidation reactor lines in both stages was replaced by a corresponding but fresh catalyst charge. The procedure of Comparative Example 1 was then continued. The results achieved after the interruption as a function of the operating time (weeks) are shown by Table 2.

TABLE 2

| Operating time | $S^{AA}$ | $S^{HAc}$ | $S^F$ | V |
|---|---|---|---|---|
| Startup | 89 | 1.7 | 1.0 | 52.4 |
| 4 | 89.6 | 1.6 | 0.9 | 56 |
| 8 | 89.9 | 1.6 | 0.9 | 56.2 |
| 12 | 90.2 | 1.6 | 0.9 | 56.4 |
| 16 | 90.5 | 1.5 | 0.8 | 60.3 |
| 20 | 90.7 | 1.5 | 0.8 | 60.5 |
| 24 | 91.0 | 1.5 | 0.8 | 60.7 |
| 28 | 91.2 | 1.5 | 0.8 | 60.8 |

The further separation of the aqueous, target product-comprising absorbate has to be designed only for a ratio of V=52.4.

Comparative Example 2

Comparative Example 1 was repeated (except that the dilution selected in section B of the second reaction stage was 40% by weight), but the composition of the charge mixture for the first reaction stages was selected as follows:
- 7.3% by volume of propene,
- 10% by volume of water,
- 0.7% by volume of constituents other than propene, water, oxygen and nitrogen,
- molecular oxygen in an amount such that the molar ratio of molecular oxygen comprised to propene comprised was 1.73, and
- as the remainder to 100% by volume, molecular nitrogen.

Secondary air was not metered in. The starting reaction gas mixture comprised 3.5% by volume of cycle gas per % by volume of fresh propene.

Table 3 comprises the results which resulted as a function of the operating time (in weeks).

TABLE 3

| Operating time | $S^{AA}$ | $S^{Hac}$ | $S^F$ | V |
|---|---|---|---|---|
| Startup | 86.7 | 2.25 | 1.35 | 38.5 |
| 4 | 87.9 | 2.15 | 1.25 | 40.9 |
| 8 | 88.7 | 2.05 | 1.2 | 43.3 |
| 12 | 89.3 | 2 | 1.1 | 44.7 |
| 16 | 89.5 | 1.95 | 1.05 | 45.9 |
| 20 | 90.1 | 1.9 | 1 | 47.4 |
| 24 | 90.3 | 1.87 | 0.97 | 48.3 |
| 28 | 90.6 | 1.85 | 0.95 | 49.0 |

The further separation of the aqueous, target product-comprising absorbate has to be designed for a ratio of V=38.5.

Example 2

First, Comparative Example 2 was repeated. After the repetition of Comparative Example 2 had produced 2200 kg of acrylic acid without interruption, operation was interrupted and only the catalyst charge of one of the two oxidation reactor lines in both stages was replaced by a corresponding but fresh catalyst charge. The procedure of Comparative Example 2 was then continued. The results achieved after the interruption as a function of the operating time (weeks) are shown by Table 4.

TABLE 4

| Operating time | $S^{AA}$ | $S^{Hac}$ | $S^F$ | V |
|---|---|---|---|---|
| Startup | 88.8 | 2.1 | 1.2 | 42.3 |
| 4 | 89.4 | 2.0 | 1.1 | 44.7 |
| 8 | 89.8 | 1.9 | 1.1 | 47.3 |
| 12 | 90.1 | 1.9 | 1.0 | 47.4 |
| 16 | 90.2 | 1.9 | 1.0 | 47.5 |
| 20 | 90.5 | 1.8 | 1.0 | 50.3 |
| 24 | 90.6 | 1.8 | 0.9 | 50.3 |
| 28 | 90.8 | 1.8 | 0.9 | 50.4 |

The further separation of the aqueous, target product-comprising absorbate has to be designed only for a ratio of V=42.3.

An apparatus comprising two oxidation reactor systems which are charged with catalysts which are suitable for the preparation of an organic target compound by heterogeneously catalyzed partial oxidation of an organic precursor compound and at whose outlet is disposed in each case a line for the removal of the product gas stream comprising the target compound from the particular oxidation reactor system, which lines are combined with increasing distance from the two oxidation reactor systems to give a product gas line which leads to an apparatus in which the product gas stream can be condensed partly or fully, wherein the catalyst charge of one of the two oxidation reactor systems comprises at least one portion of catalyst over which more target product has already been generated than over the portions of catalyst of the catalyst charge of the other oxidation reactor system, is suitable for carrying out the process according to the invention.

Processes including a process for preparing at least one organic target compound by heterogeneously catalyzed gas phase partial oxidation of at least one organic precursor compound with molecular oxygen in at least two oxidation reactor systems which comprise catalyst charges and are operated in parallel to obtain at least two product gas streams each comprising the target compound and each stemming from one of the at least two oxidation reactor systems, wherein an overall stream of starting reaction gas mixture comprising the at least one organic precursor compound is initially obtained and this is subsequently fed via a distributor system to the at least two oxidation reactor systems operated in parallel, with the proviso that at least one of the catalyst charges of the at least two oxidation reactor systems operated in parallel comprises at least one portion of catalyst over which the heterogeneously catalyzed gas phase partial oxidation has already been carried out for longer than over all portions of catalyst of the at least one other catalyst charge; or the above process wherein the at least one of the catalyst charges of the at least two oxidation reactor systems operated in parallel comprises at least one portion of catalyst over which the heterogeneously catalyzed gas phase partial oxidation has already been carried out for at least 30 calendar days longer than over all portions of catalyst of the at least one other catalyst charge; or any of the above processes wherein the at least one organic precursor compound is propylene, isobutene, ethylene, ethane, propane, isobutane, acrolein, methacrolein, butadiene, o-, m-, p-xylene and/or naphthalene; or any of the above processes wherein the heterogeneously catalyzed gas phase partial oxidation is the two-stage heterogeneously catalyzed partial oxidation of propene to acrylic acid; or any of the above processes wherein the heterogeneously catalyzed gas phase partial oxidation is the one-stage heterogeneously catalyzed partial oxidation of propane to acrylic acid; or any of the above processes wherein the at least two oxidation reactor systems operated in parallel consist of two tandem tube bundle reactor arrangements operated in parallel; or any of the above processes wherein the catalysts of the first reaction stage are multimetal oxide compositions comprising Mo, Bi and Fe, and the catalysts of the second reaction stage are multimetal oxide compositions comprising Mo and V, form, for example, the basis for an application of the inventive procedure.

U.S. Provisional Patent Application Nos. 60/656,881, filed on Mar. 1, 2005, and 60/670,289, filed on Apr. 12, 2005, are incorporated into the present application by literature reference. With regard to the abovementioned teachings, numerous alterations and deviations from the present invention are possible. It can therefore be assumed that the invention, within the scope of the appended claims, can be performed in a different way from that specifically described herein.

What is claimed is:

1. An apparatus comprising two oxidation reactor systems which are charged with catalysts which are suitable for the preparation of an organic target compound by heterogeneously catalyzed partial oxidation of an organic starting material compound and at whose outlet is disposed in each case a line for the removal of the product gas stream comprising the target compound from the particular oxidation reactor system, which lines are combined with increasing distance from the two oxidation reactor systems to give a product gas line which leads to an apparatus in which a product mixed gas contained in said product gas line can be condensed partly or fully, wherein the catalyst charge of one of the two oxidation reactor systems comprises at least one portion of catalyst over which more target product has already been generated than over all portions of catalyst of the catalyst charge of the other oxidation reactor system.

2. The apparatus according to claim 1, wherein the two oxidation reactor systems are configured to operate in parallel, and to remove the target compound from a mixture stream of the two product streams.

3. The apparatus according to claim 1, wherein the two oxidation reactor systems are configured to operate the heterogeneously catalyzed gas phase partial oxidation as a two-stage heterogeneously catalyzed partial oxidation of propane to acrylic acid.

4. The apparatus according to claim 1, wherein the two oxidation reactor systems are configured to operate the heterogeneously catalyzed gas phase partial oxidation as a one-stage heterogeneously catalyzed partial oxidation of propane to acrylic acid.

5. The apparatus according to claim 1, wherein the two oxidation reactor systems are configured to operate the heterogeneously catalyzed gas phase partial oxidation as a two-stage heterogeneously catalyzed partial oxidation of isobutene to methacrylic acid.

6. The apparatus according to claim 1, wherein the two oxidation reactor systems are configured to operate in parallel and consist of two tandem tube bundle reactor arrangements operated in parallel.

7. The apparatus according to claim 1, additionally comprising a column configured for a fractional condensation of the mixed product gas.

8. The apparatus according to claim 1, additionally comprising a column configured for an absorption of target product from the mixed product gas.

* * * * *